US011000218B2

(12) United States Patent
Misra et al.

(10) Patent No.: US 11,000,218 B2
(45) Date of Patent: May 11, 2021

(54) SYSTEMS AND METHODS FOR DYNAMICALLY PROVIDING AND DEVELOPING BEHAVIORAL INSIGHTS FOR INDIVIDUALS AND GROUPS

(71) Applicants: Raghavendra Misra, Ponte Vedra, FL (US); Rohan Misra, Ponte Vedra, FL (US)

(72) Inventors: Raghavendra Misra, Ponte Vedra, FL (US); Rohan Misra, Ponte Vedra, FL (US)

( * ) Notice: Subject to any disclaimer, the term of this patent is extended or adjusted under 35 U.S.C. 154(b) by 0 days.

(21) Appl. No.: 17/000,222

(22) Filed: Aug. 21, 2020

(65) Prior Publication Data

US 2021/0052204 A1 Feb. 25, 2021

Related U.S. Application Data

(60) Provisional application No. 62/890,526, filed on Aug. 22, 2019, provisional application No. 62/890,552, filed on Aug. 22, 2019.

(51) Int. Cl.
*A61B 5/16* (2006.01)
*G06F 16/904* (2019.01)
*G06F 16/9035* (2019.01)

(52) U.S. Cl.
CPC .............. *A61B 5/16* (2013.01); *G06F 16/904* (2019.01); *G06F 16/9035* (2019.01)

(58) Field of Classification Search
CPC ...... A61B 5/16; G06F 16/904; G06F 16/9035
USPC ......................................................... 707/733
See application file for complete search history.

(56) References Cited

U.S. PATENT DOCUMENTS

| | | | | |
|---|---|---|---|---|
| 9,430,570 B2* | 8/2016 | Button | ................... | G06N 5/022 |
| 10,409,915 B2* | 9/2019 | Buckwaiter | ......... | G06F 16/9535 |
| 2004/0219493 A1* | 11/2004 | Phillips | ................... | G09B 5/06 |
| | | | | 434/118 |
| 2005/0096973 A1* | 5/2005 | Heyse | ................... | G06Q 50/10 |
| | | | | 705/7.39 |
| 2009/0100032 A1* | 4/2009 | Jones | ................... | G06F 16/9535 |
| 2012/0102050 A1* | 4/2012 | Button | ............... | G06F 16/9535 |
| | | | | 707/749 |
| 2012/0196255 A1* | 8/2012 | Clarke | ................... | A63B 24/00 |
| | | | | 434/236 |
| 2012/0284080 A1* | 11/2012 | De Oliveira | ....... | G06Q 30/0202 |
| | | | | 705/7.29 |
| 2012/0330869 A1* | 12/2012 | Durham | ................. | G06N 5/022 |
| | | | | 706/16 |
| 2013/0006685 A1* | 1/2013 | Kelkar | ................... | G06Q 10/00 |
| | | | | 705/7.11 |

(Continued)

OTHER PUBLICATIONS

Caddle, Xavier V., "PSYCH: An Extensible Framework for Psychometric Detecion Using Speech to Text", Thesis, Univ. of the West Indies at Cave Hill, Barbados, Aug. 2013, 100 pages.*

*Primary Examiner* — Robert Stevens
(74) *Attorney, Agent, or Firm* — Camille A. Wilson; Wilson Dutra, PLLC

(57) ABSTRACT

The present disclosure provides generally for providing behavioral insights across individuals and groups and presenting this information in a clear, actionable, and reliable way. The method and system may efficiently and effectively assess individuals and groups using a variety of factors, such as with psychometric assessments. Accordingly, the present disclosure relates to systems and methods for providing dynamic behavioral insights for individuals and groups.

14 Claims, 26 Drawing Sheets

(56) References Cited

U.S. PATENT DOCUMENTS

| | | | |
|---|---|---|---|
| 2013/0282605 A1* | 10/2013 | Noelting | G06Q 10/10 |
| | | | 705/321 |
| 2014/0136089 A1* | 5/2014 | Hranac | G08G 1/096775 |
| | | | 701/118 |
| 2014/0358586 A1* | 12/2014 | Patel | H04N 19/00 |
| | | | 705/3 |
| 2015/0026149 A1* | 1/2015 | Jones | G06Q 30/0224 |
| | | | 707/706 |
| 2015/0199746 A1* | 7/2015 | Hocking, Jr. | G06Q 40/06 |
| | | | 705/26.7 |
| 2015/0279227 A1* | 10/2015 | Huber | G09B 7/02 |
| | | | 434/353 |
| 2016/0103872 A1* | 4/2016 | Prophete | G06Q 10/0639 |
| | | | 707/722 |
| 2017/0147984 A1* | 5/2017 | Zoia | G06F 16/9535 |
| 2018/0114457 A1* | 4/2018 | Liethen | G09B 7/02 |
| 2018/0188903 A1* | 7/2018 | Sirpal | G06F 3/0482 |
| 2018/0366021 A1* | 12/2018 | Zertuche | G06F 40/40 |
| 2019/0102802 A1* | 4/2019 | Tuschman | G06F 16/313 |

* cited by examiner

FIG. 3

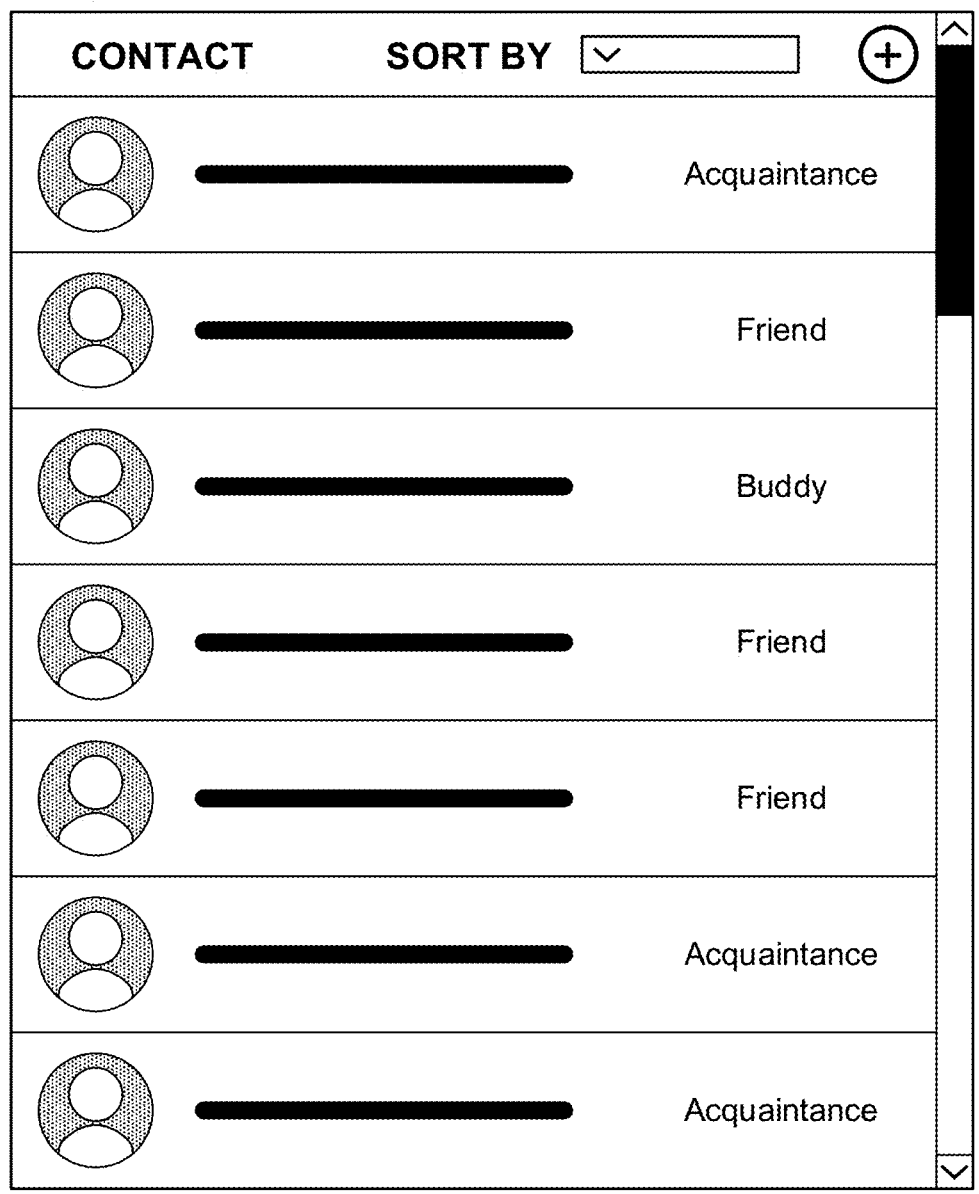

FIG. 5B

Network Dashboard

| CONTACT | ACQUAINTANCE | FRIEND | BUDDY |
|---|---|---|---|
| 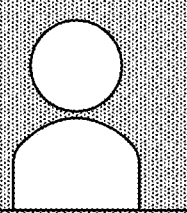 | ✓ Basic Profile page<br>✓ Some behavior info | ✗ Full Profile page<br>✗ Most behavior info<br>✗ Connections | ✗ All behavior info<br>✗ All insights |
| 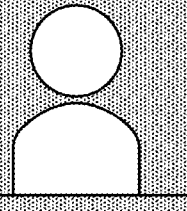 | ✓ Basic Profile page<br>✓ Some behavior info | ✓ Full Profile page<br>✓ Most behavior info<br>✓ Connections | ✗ All behavior info<br>✗ All insights |
| 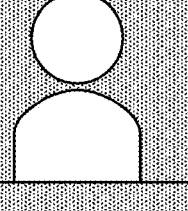 | ✓ Basic Profile page<br>✓ Some behavior info | ✓ Full Profile page<br>✓ Most behavior info<br>✓ Connections | ✓ All behavior info<br>✓ All insights |
| 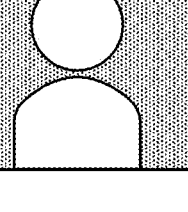 | ✓ Basic Profile page<br>✓ Some behavior info | ✗ Full Profile page<br>✗ Most behavior info<br>✗ Connections | ✗ All behavior info<br>✗ All insights |

FIG. 7 Team Overview/Dashboard
    
  
  

FIG. 8A

| Team Member | Behavior Factors | Performance Keys | Communication Style |
|---|---|---|---|
| Employee A | Initiator, Spontaneous, Creative | Provide broad factors Encourage brainstorming | Move at fast pace Provide options Provide visuals |
| Employee B | Adaptor, Reserved, Anchored | Allow reflection time Keep it tangible | Provide logical steps Provde details |
| Employee C | | Need Information | |
| Employee D | | Need Information | |

FIG. 8B

SYSTEMS AND METHODS FOR DYNAMICALLY PROVIDING AND DEVELOPING BEHAVIORAL INSIGHTS FOR INDIVIDUALS AND GROUPS

CROSS-REFERENCE TO RELATED APPLICATION

This application claims priority to and the full benefit of U.S. Provisional Patent Application Ser. No. 62/890,526, filed Aug. 22, 2019, and titled "SYSTEMS AND METHODS FOR DYNAMICALLY PROVIDING AND DEVELOPING BEHAVIORAL INSIGHTS FOR INDIVIDUALS AND GROUPS" and U.S. Provisional Patent Application Ser. No. 62/890,552, filed Aug. 22, 2019, and titled "SYSTEMS AND METHODS FOR DYNAMICALLY RECEIVING AND PROVIDING PERSONNEL REVIEW DATA BASED ON BEHAVIORAL INSIGHTS", the entire contents of which are incorporated in this application by reference.

BACKGROUND OF THE DISCLOSURE

Psychometrics were developed as a method for measuring psychological attributes or abilities, typically through an assessment. The study of psychometrics includes the study of the statistical, mathematical, and professional protocols that underpin any assessment used and how any assessment is constructed, used, and evaluated.

Some of the very first instances of mental testing started in ancient China, where proficiency assessments were used to grade, rank, and place personnel. These early assessments were a mix of skill, intelligence, and endurance testing, often requiring a candidate to attend testing for a full day and night. At the time, these exams had incredibly low passage rates, with a stated goal of only finding the best personnel for public official positions.

In the 13$^{th}$ century, European universities gave students formal oral testing, with written examinations starting in the 16$^{th}$ century. By the beginning of the 19$^{th}$ century, competitive university examinations were instituted. As social mobility increased, society relied more on other forms of assessments to determine who was appropriate for certain roles, such as in the government. This switch from personal judgment or word of mouth to something more impartial helped streamline application processes and vetting for whether a person was fit for a position or role in a group. This led to an academic interest in human variation and measurement-based psychology.

The interest in measuring behavioral capacity and mental capabilities has expanded to determining who might be appropriate when building a team within an organization. A version of a psychometric assessment might be useful when determining a culture fit or how to best optimize the makeup of a team. For example, these assessments may vary and test for aptitude, ability, or personality. Employers may use these at any phase of an employee's life cycle within a company, from onboarding, determining fit, and future potential, such as for a promotion or working in a different department or specialty.

One particular focus of psychometrics is providing objective and impersonal assessments for individuals or groups to be compared without unconscious bias. Despite the advancements made standardizing and optimizing assessments within an organization, there is always room for increased efficiency when implementing or reviewing psychometric assessments.

SUMMARY OF THE DISCLOSURE

What is needed is a method and system for providing behavioral insights across individuals and groups and presenting this information in a clear, actionable, and reliable way. The method and system may efficiently and effectively assess individuals and groups using a variety of factors, such as with psychometric assessments. Accordingly, the present disclosure relates to systems and methods for providing dynamic behavioral insights for individuals and groups.

In some embodiments, a system of one or more computers may be configured to perform particular operations or actions by virtue of having software, firmware, hardware, or a combination of them installed on the system that in operation causes or cause the system to perform the actions. In some aspects, one or more computer programs may be configured to perform particular operations or actions by virtue of including instructions that, when executed by data processing apparatus, cause the apparatus to perform the actions. In some implementations, the present disclosure may comprise a method for providing behavioral insights. In some aspects, the method may comprise receiving at least one psychometric profile of a subject; creating a subject profile; developing subject behavioral insights for the subject based on processing the at least one psychometric profile, the interest list, and the skill list; building a subject dashboard may comprise a visualization of subject behavioral insights; storing the at least one psychometric profile, the interest list, the skill list, and subject behavioral insights, and the subject dashboard with the subject profile; and providing the subject dashboard to a user. the method wherein the user may comprise the subject, and the subject's dashboard is customized based on subject behavioral insights. the method may comprise integrating with an external communication system, wherein at least a portion of the subject dashboard is visible when communicating with the subject through the external communication system. In some embodiments, this may include corresponding computer systems, apparatus, and computer programs recorded on one or more computer storage devices, each configured to perform the actions of the methods.

In some implementations, the method may comprise one or more receiving an aspiration list of the subject, wherein the aspiration list may comprise at least one aspiration and date as the aspiration list may comprise at least one aspiration and date associated with at least one aspiration; receiving an interest list of the subject, wherein the interest list may comprise at least one interest and date associated with at least one interest; and receiving a talent list of the subject, wherein the talent list may comprise at least one talent and date associated with at least one talent.

In some embodiments, the method may comprise receiving one or more updated aspiration list, updated interest list, or updated talent list, wherein the subject dashboard may comprise an animation indicating one or more progression of the aspiration list to the updated aspiration list, the interest list to the updated interest list, and the talent list to the updated talent list. In some aspects, the method may comprise receiving a skill list of the subject, wherein the skill list may comprise at least one skill, a skill level of at least one skill, and a skill time range associated with the skill level. In some implementations, the method may comprise receiving an updated skill list and comparing the updated skill list to the skill list, wherein the updated skill list may comprise at least the updated skill, an updated skill level for at least one update skill, an updated skill time range associated with the updated skill level, wherein the subject dashboard is updated to reflect the updated skill list. In some aspects, the subject dashboard may comprise an animation indicating a progression of the skill list to the updated skill list.

In some implementations, the behavioral insights dashboard may comprise a visualization of subject performance data, wherein the visualization is based at least in part on subject behavioral insights. In some aspects, the method may comprise receiving updated performance data, wherein the subject dashboard may comprise an animation indicating a progression of the subject performance data to the updated performance data. In some implementations, a method for providing behavioral insights for a group may comprise receiving a plurality of psychometric profiles for a group, wherein the group may comprise a plurality of group members, and wherein at least one of the pluralities of psychometric profiles relates to each group member; creating a group profile. In some aspects, the skill list is compiled from group member skills list; developing group behavioral insights based at least on processing of the plurality of psychometric profiles; and providing a behavioral insights dashboard may comprise an implementation of the described techniques may include hardware, a method or process, or computer software on a computer-accessible medium.

In some aspects, the present disclosure may comprise providing a behavioral insights dashboard which may comprise a visualization of behavioral insights. In some embodiments, the method may comprise the method wherein the group behavioral insights are further based on the group skill list, wherein the plurality of psychometric profiles change as the plurality of group members changes, and wherein group behavioral insights are updated in real time as plurality of group members changes. In some implementations, the method may comprise recommending changes to the plurality of group members based on behavioral insights. the method wherein recommending is based on a balance assessment of group behavioral insights. In some aspects, this may include corresponding computer systems, apparatus, and computer programs recorded on one or more computer storage devices, each configured to perform the actions of the methods.

In some implementations, one or more of the following features of the method may comprise integrating with an external communication system, wherein at least a portion of one or both group behavioral insights and group member behavioral insights are provided when communicating with one or both the group or group members. In some embodiments, a method of sharing behavioral insights may comprise receiving. In some aspects, the described techniques may include hardware, a method or process, or computer software on a computer-accessible medium.

In some embodiments, the present disclosure may comprise receiving a first sharing request from the first subject for a second subject. In some aspects, the method of sharing behavioral insights may comprise providing at least a portion of segments from the first subject dashboard to the second subject, wherein at least the portion of segments may comprise visibility values less than the first threshold visibility value. In some implementations, the method may comprise receiving at least a second psychometric profile of the second subject and a second skill list, developing a second set of behavioral insights based on at least the second psychometric profile and the second skill list, creating a second subject profile may comprise at least a second subject name and the first set of behavioral insights, generating a second subject dashboard may comprise a second visualization of at least a portion of the second set of behavioral insights, wherein the second visualization is provided in a second plurality of segments, assigning visibility values to the first plurality of segments and the second plurality of segments, wherein visibility values indicate privacy levels of each of the first plurality of segments and the second plurality. In some embodiments, this may include corresponding computer systems, apparatus, and computer programs recorded on one or more computer storage devices, each configured to perform the actions of the methods.

In some implementations, one or more of the following features are assigning visibility values to the first plurality of segments and the second plurality of segments, wherein visibility values indicate privacy levels of each of the first plurality of segments and the second plurality of segments; receiving a second sharing request from the second subject for the first subject, wherein the second sharing request indicates a second threshold visibility value, wherein at least a portion of the second plurality of segments with visibility values below the second threshold visibility value are visible to the first subject; and providing at least a portion of segments from the second subject dashboard to the first subject, wherein the least the portion of segments may comprise visibility values less than the second threshold visibility value. the method wherein the first threshold visibility value and the second threshold visibility value are different. the method may comprise integrating with an external communication system. the method wherein at least a portion of the portion of segments of the first set of behavioral insights is visible to the second subject when the second subject communicates with the first subject through the external communication system. abstract the present disclosure provides generally for providing behavioral insights across individuals and groups and presenting this information in a clear, actionable, and reliable way. the method and system may efficiently and effectively assess individuals and groups using a variety of factors, such as with psychometric assessments. In some embodiments, the present disclosure provides generally for providing behavioral insights across individuals and groups and presenting this information in a clear, actionable, and reliable way. the method and system may efficiently and effectively assess individuals and groups using a variety of factors, such as with psychometric assessments. In some aspects, present disclosure relates to systems and methods for providing dynamic behavioral insights for individuals generating a first subject dashboard may comprise a first visualization of at least a portion of the first set of behavioral insights, wherein the first visualization is provided in a first plurality of segments. In some embodiments, the method includes assigning visibility values to the first plurality of segments, wherein visibility values indicate privacy levels of each of the first plurality of segments; receiving a first sharing request from the first subject for a second In some implementations of the described techniques may include hardware, a method or process, or computer software on a computer-accessible medium.

In some implementations, comprise one or more of the following features generating a first subject dashboard which may comprise a first visualization of at least a portion of the first set of behavioral insights, wherein the first visualization is provided in a first plurality of segments. In some aspects, the method includes assigning visibility values to the first plurality of segments, wherein visibility values indicate privacy levels of each of the first plurality of segments; receiving a first sharing request from the first subject for a second In some embodiments of the described techniques may include hardware, a method or process, or computer software on a computer-accessible medium.

BRIEF DESCRIPTION OF THE DRAWINGS

The accompanying drawings, that are incorporated in and constitute a part of this specification, illustrate several embodiments of the disclosure and, together with the description, serve to explain the principles of the disclosure:

FIG. 3 illustrates an exemplary team report dashboard, according to some embodiments of the present disclosure.

FIG. 5A illustrates an exemplary network behavioral insight dashboard, according to some embodiments of the present disclosure.

FIG. 5B illustrates an exemplary network behavioral insight dashboard, according to some embodiments of the present disclosure.

FIG. 7 illustrates an exemplary team composition dashboard, according to some embodiments of the present disclosure.

FIG. 8A illustrates exemplary illustrative behavioral insights for a team, wherein the behavioral insights are based at least in part on psychometric profiles.

FIG. 8B illustrates exemplary text behavioral insights for a team, wherein the behavioral insights are based at least in part on psychometric profiles.

DETAILED DESCRIPTION

The present disclosure provides generally for providing behavioral insights across individuals and groups and presenting this information in a clear, actionable, and reliable way. The method and system may efficiently and effectively assess individuals and groups using a variety of factors, such as with psychometric assessments. Accordingly, the present disclosure relates to systems and methods for providing dynamic behavioral insights for individuals and groups.

In the following sections, detailed descriptions of examples and methods of the disclosure will be given. The description of both preferred and alternative examples though thorough are exemplary only, and it is understood that to those skilled in the art variations, modifications, and alterations may be apparent. It is therefore to be understood that the examples do not limit the broadness of the aspects of the underlying disclosure as defined by the claims.

GLOSSARY

Behavioral Insight: as used herein refers to characteristics and attributes associated with a person, persons, or groups. In some embodiments, the characteristics and attributes may be a combination of psychometric profile, interests, aspirations, talents, and skills, as non-limiting examples. In some aspects, behavioral insights may consider performance data, feedback data, historical data, user-generated data, or combinations thereof. In some aspects, the behavioral insight may be applied to business roles, personal roles, academic roles, or any other role where understanding behavior may be useful. For example, a life coach may use behavioral insights to inform how to coach a user. As another example, an employer may use behavioral insights to understand and improve team dynamics.

Psychometric Profile: as used herein refers to a set of psychometric attributes associated with a person, persons, or groups based on actual psychometric assessments, historical psychometric assessments associated with a demographic, implied psychometric attributes based on behavior, or combinations thereof.

Subject: as used herein refers to a person or group who is the subject of a psychometric profile, behavioral insights, feedback, or performance data, as non-limiting examples.

Figure 1A:
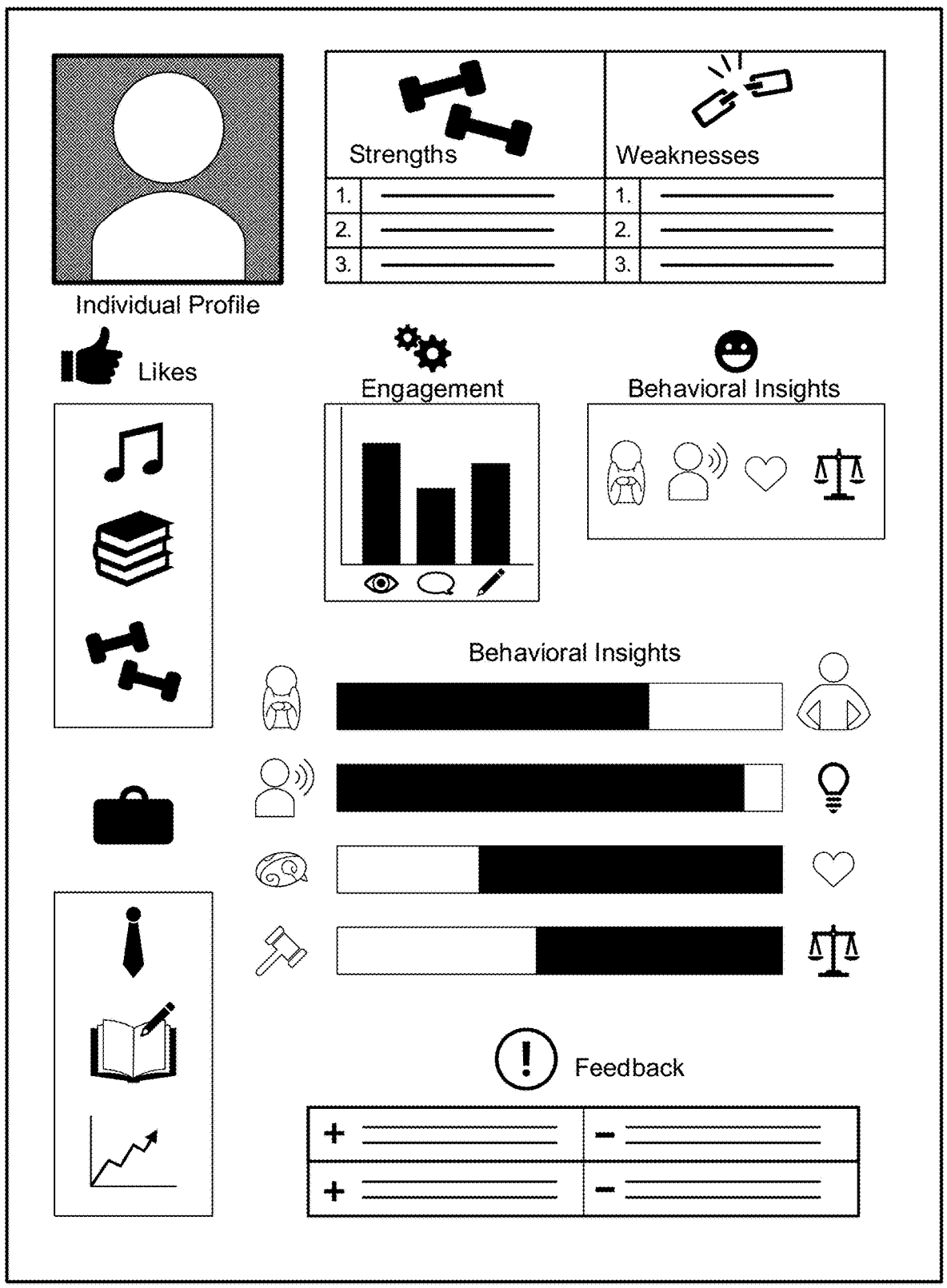
FIG. 1A illustrates an exemplary individual behavioral insight dashboard, according to some embodiments of the present disclosure.
Figure 1B:
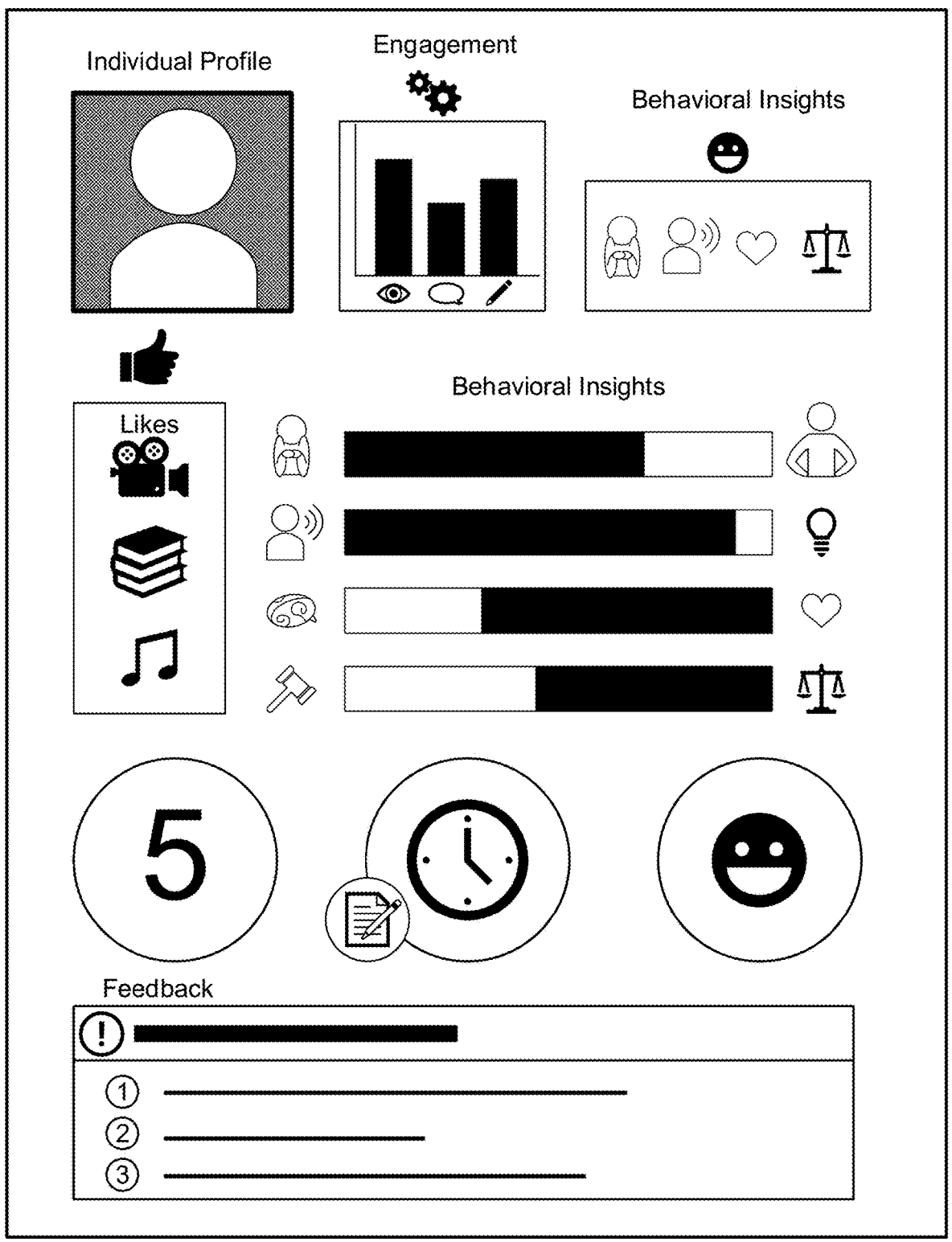
FIG. 1B illustrates an exemplary individual behavioral insight dashboard, according to some embodiments of the present disclosure.
Figure 1C:
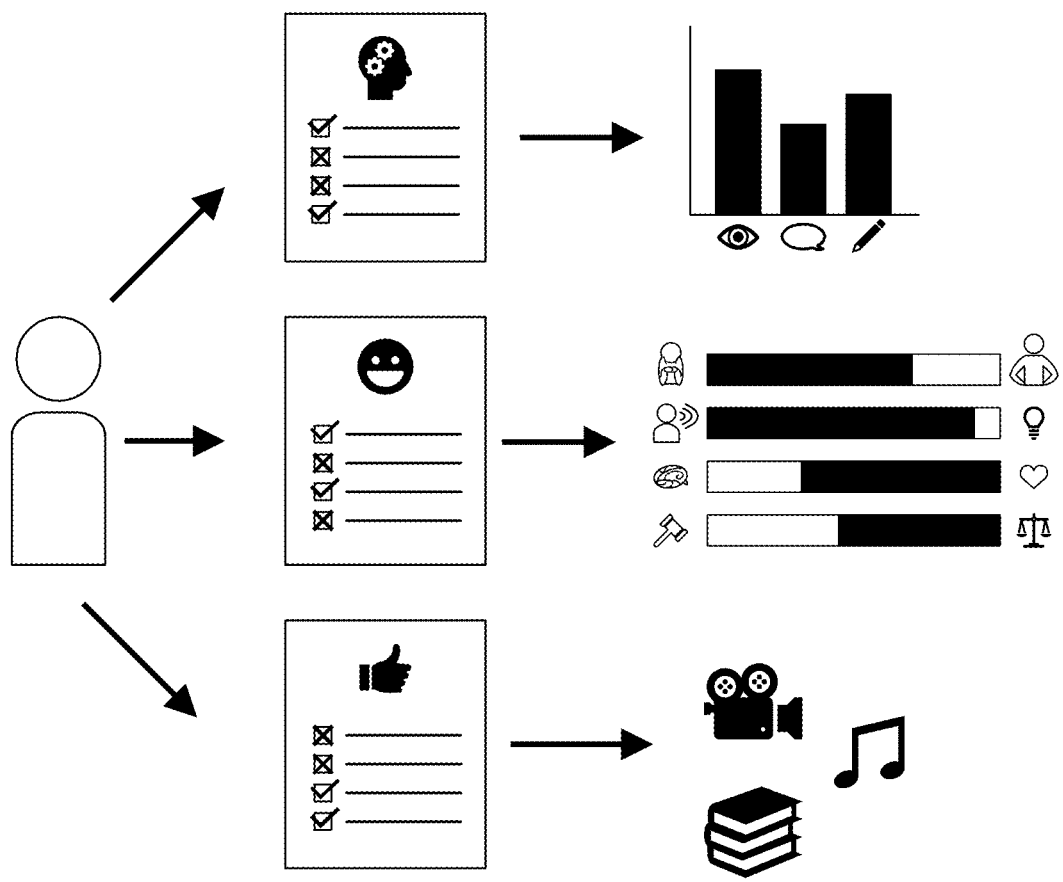
FIG. 1C illustrates an exemplary data collection flow for generating behavioral insights for an individual.
Figure 1D:
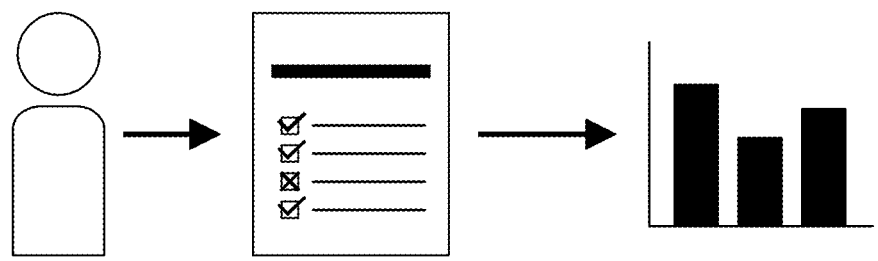
FIG. 1D illustrates an exemplary data collection flow for generating behavioral insights for an individual.
Figure 1E:
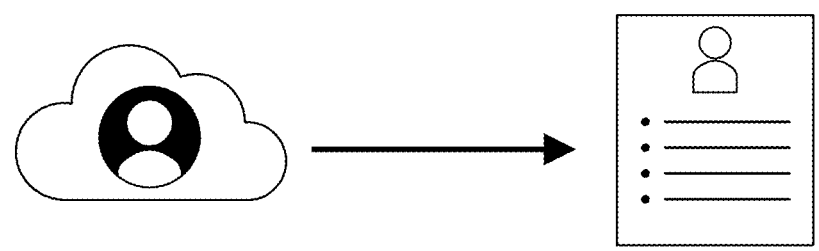
FIG. 1E illustrates an exemplary data collection flow for generating behavioral insights for an individual.
Figure 1F:
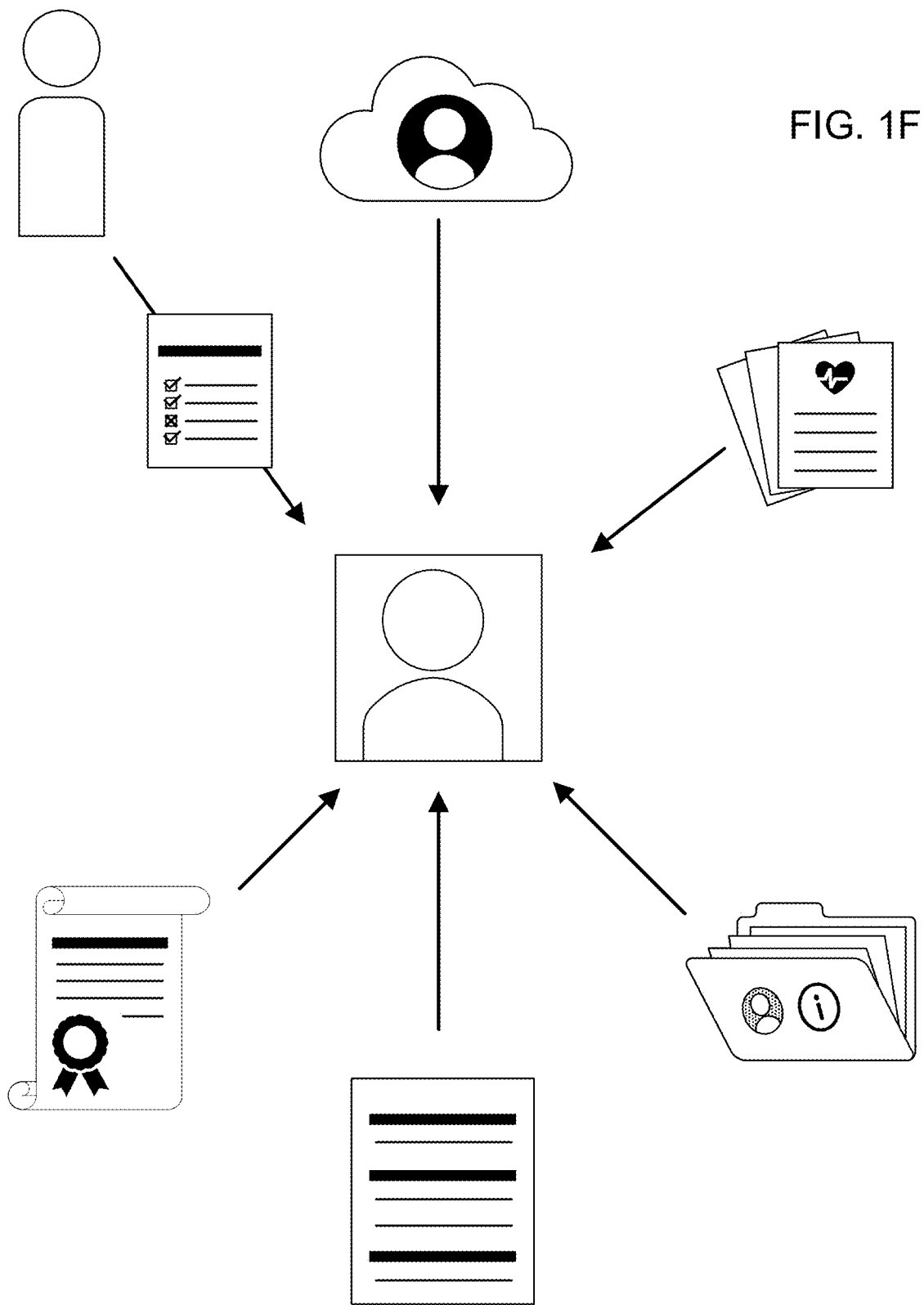
FIG. 1F illustrates an exemplary data collection flow for generating behavioral insights for an individual.

Referring now to FIGS. 1A and 1i, an exemplary behavioral insight dashboard is illustrated. In some embodiments, the behavioral insight dashboard may present behavioral insights in graphic form, which may include illustrations of potential psychometric profile permutations. In some aspects, the behavioral insight dashboard may provide a high level understanding of a workforce over time. In some implementations, understanding trends of the aggregated psychometric profiles of the workforce may be useful. In some aspects, the aggregated behavioral insights and psychometric profiles may be correlated and compared to other historical data, such as performance data, feedback data, customer reviews, valuations, sales, or employee turnover, as non-limiting examples.

In some aspects, a psychometric profile may be associated with an individual, which may be generated through a directed psychometric assessment, personal data, tracked activities, third party feedback, training, education, certifications, test results, experience, interests, or combinations thereof. In some implementations, a psychometric profile may be associated with a group, such as a team, a workforce, c-suite, position, or role. In some embodiments, the group psychometric profile may comprise an aggregation, extrapolation, average, or other combination of the individual psychometric profiles.

In some implementations, scores for different attributes, such as team effectiveness score, c-suite score, leader score, position score (for a specific position in a company), may be generated based at least in part on a psychometric profile. In some aspects, the psychometric profile may be combined with other data, such as performance data, feedback data, interests, aspirations, skills, or experience, as non-limiting examples.

In some embodiments, a real-time assessment of the company climate may be generated, such as generally content, anxious, discontent, suspicious, trusting, or loyal, as non-limiting examples. In some aspects, the climate may be assessed by overall employees, team, position, or role, as non-limiting examples. In some implementations, suggestions on how to improve scores and climate may be provided based on the psychometric profiles and behavioral insights of the individuals and groups.

In some aspects, the scores and graphs may be used to group specific users together based on similar scores or attributes. In some embodiments, results may be used to guide performance review suggestions or recommend improvements for subjects lacking certain skills.

In some implementations, company climate may apply to a college, wherein the climate of the students may be assessed. In some aspects, the students may be broken into groups based on a predefined commonality, such as by year, course, professor, resident advisor, extracurricular activity, club associations, or sport, as non-limiting examples. Group climates may allow for a deeper understanding of the students that may have more authentic results than other assessment methods, such as surveys. In some embodiments, survey data may be combined with group climate data.

For example, a group climate for students taking organic chemistry may be comparable to the entire student body, but when the groups are further broken down by professor, student climate from one professor may be skewed negative. The negative climate may draw attention to the group, and surveys may provide additional insight, such as the professor does not explain assignments or the grading is inconsistent. Based on the feedback and climate, the university may look into the psychometric profiles of the students in that class and compare it to the professor's psychometric profile, curriculum, and teaching style. The comparison may provide insight as to why the climate for that particular class may be low.

Referring now to FIGS. 1C-1F, exemplary data collection flow for generating behavioral insights for an individual is illustrated. In some embodiments, data may be gathered using different categories grouped together to form datapoints. For example, the three sets of data may be used to generate one graph of data based on all the information gathered. In some aspects, each individual data gathered may generate its own graph rather than being combined into one.

In some implementations, personality data, attitude patterns, and feedback data may feed into the data charts that are related to the user. In some embodiments, rather than observing data the user may directly input the system data. In some embodiments, the user may be required to take more than one assessment for each data requirement or section for the system. For example, the user may need to take a personality assessment as well as an assessment about their behaviors in situations.

In some implementations, the system may comprise a cloud system that may store a portion or all information from users. For example, a specific profile may be pulled from the cloud at any point and all of the data may be saved to the profile for easy access. In some embodiments, the cloud may be updated periodically or in real time when new information or data arises for any profile in the cloud. In some aspects, the cloud may be accessed from any mobile device or computer with internet access. In some implementations, only a portion of the data may be stored with the cloud system, wherein the system may interface with external systems and databases to complete subject and group profiles. For example, the system may store behavioral insights, aspirations, skills, and feedback for a subject or group, and then periodically interface with social media or communication systems for supplemental data.

In some embodiments, the user profile may track educational history, such as from high school or college. In some aspects, the educational history may include test grades, final grades, paper submissions, and peer reviews, as non-limiting examples. In some implementations, the history may be tracked even through graduation and into the user's career. In some aspects, the profile may track each career path the user takes, their positions held, any behavioral issues and other workplace related data. In some embodiments, the subject may be reevaluated throughout the life of their profile, such as at each milestone, each new learned skill, or periodically. This may allow for current behavioral insights that may reflect the growth and development of the subject over time. In some aspects, the user profile may comprise segments that illustrate development, such as through a word tree or animation, as non-limiting examples In some aspects, the user profile may include some information from health documents. For example, where relevant and permissible, the health information may include hospital visits, medical history, and family history, as non-limiting examples. To maintain confidentiality, the health information may be used as part of a behavioral insight analysis but not overtly shared or presented in a behavioral insight dashboard. For example, an extended hospital stay due to head trauma may prompt a reevaluation. As another example, an extended illness may account for a decrease in performance or engagement.

In some aspects, a behavioral dashboard may comprise a resume segment. In some aspects, the resume segment may automatically update when any career information is added. In some aspects, the profile may take information from third parties to update any required information, such as from social media or job posting sites.

In some implementations, third parties may have the ability to comment and answer questions regarding the user profile. For example, when appropriate, if another employer has a question about work ethic or work habits, then a previous employer may answer and provide additional information. The feedback and review may be anonymous. The feedback may be analyzed a processed to eliminate superlatives or tailor the information based on behavioral insights of the further employer or the subject. In some aspects, the behavioral insights dashboard may comprise tracking segments, such as visualizations of development of aspirations, achievements, skills, and other trackable attributes or subject data.

Figure 2A:
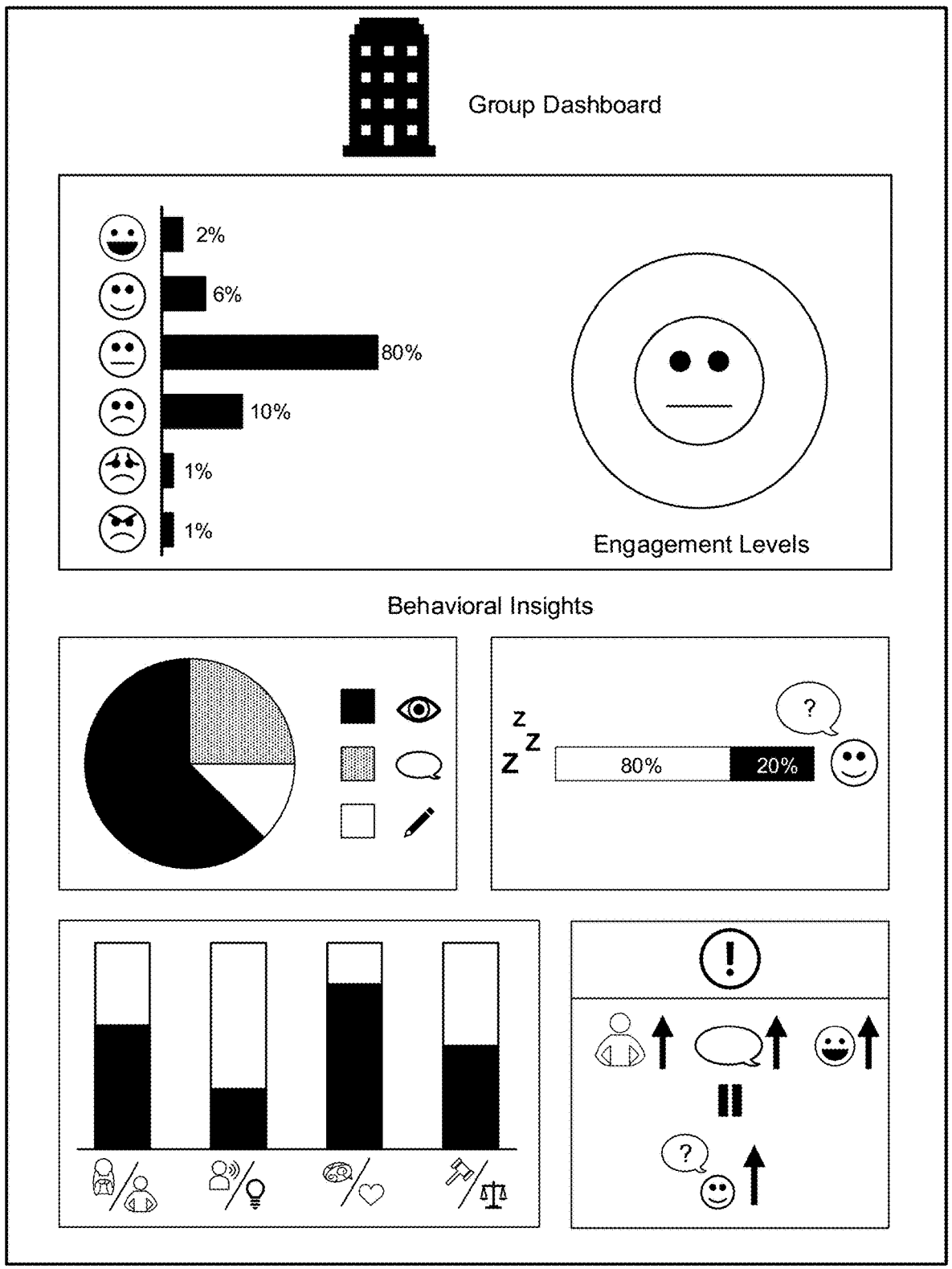
FIG. 2A illustrates an exemplary group behavioral insight dashboard, according to some embodiments of the present disclosure.

Referring now to FIG. 2A, an exemplary group behavioral insight dashboard is illustrated. In some aspects, the behavioral insight dashboard may provide an aggregated understanding of the workforce for a company. In some embodiments, the workforce may comprise employees, contractors, vendors, managers, third party service providers, or other groups or individuals that may impact the success of the company, as non-limiting examples. In some aspects, the group may comprise a student body, professors, and administrators from an educational institute, such as a college, high school, or trade school, as non-limiting examples.

For example, the behavioral insight dashboard may provide historical data in graph form tracking the level of engagement of the workforce. The level of engagement may correlate to the overall climate, wherein high engagement of the work force may indicate that the employees are content and excited to be part of the company. Low engagement may indicate that the employees are unhappy or uninterested in the company, which may suggest they are likely to leave when they find another company that may provide more satisfaction.

In some embodiments, the behavioral insight dashboard may look for specific traits to fill specific positions. In some implementations, the behavioral insight dashboard may group specific employees together for special projects or team meetings based on their psychometric profile. In some aspects, the behavioral insight dashboard may recommend subjects for certain positions based on their psychometric profile.

In some embodiments, the system may identify certain workers in third-party companies and make recommendations based on their abilities. For example, if a third-party worker is not performing well on a given task, the system may suggest a different task or job for the employee. In some aspects, the system may divide a group of people, such as students in a class or employees in a department, into balanced subsets, wherein the subsets may have comparable aggregated psychometric profiles. This may allow for an even distribution of the groups. This may allow a teacher or manager to develop a curriculum, programming, projects, or teaching style that may effectively reach each of the groups.

Figure 2B:
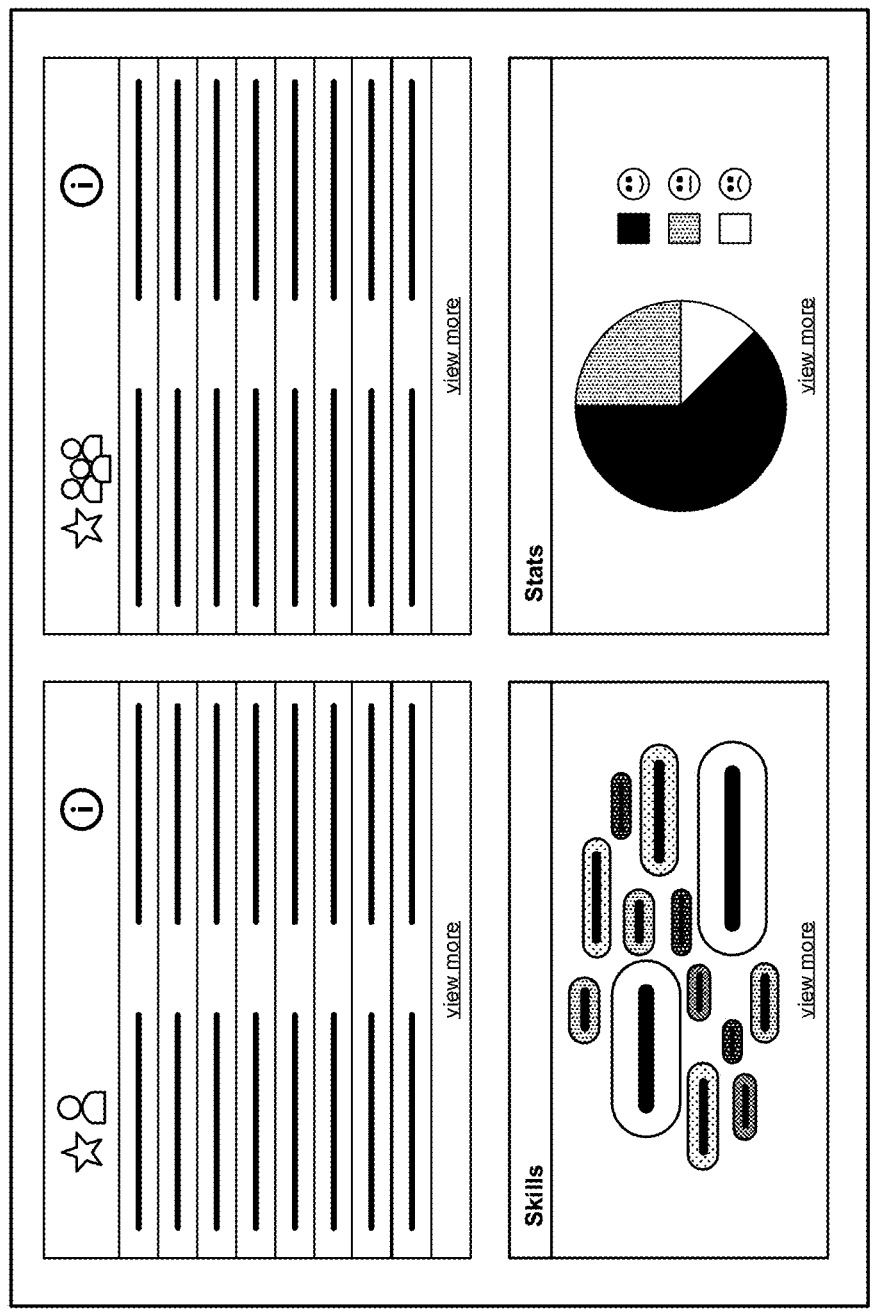
FIG. 2B illustrates an exemplary group behavioral insight dashboard, according to some embodiments of the present disclosure.

Referring now to FIG. 2B, an exemplary behavioral insight dashboard is illustrated. In some embodiments, employees or team members may be ranked based on a variety of factors, which may be customized, such as by company, skill, department, or position, as non-limiting examples. In some aspects, the behavioral dashboard may allow for sorting and filtering, which may allow for viewing of highly-customized behavioral insights and psychometric profiles.

For example, a company may want to separately assess the behavioral insights for their java developers and their sales team. The relevant metrics for understanding their psychometric profiles and behavioral insights may be distinct. Engagement for java developers may comprise attending workshops and participation in projects, and engagement for a sales team may be visiting clients and attending client events. Accordingly, ranking employees in each department may be based on different factors and the most engaged or successful employee from each group may have very different psychometric profiles.

In some aspects, the behavioral insight dashboard may recommend certain psychometric profiles or profiles to fill a board. For example, fraternities and sororities may use results to help structure their chapters' executive board. This may result in a better run organization overall because the traits may correlate to the position the member is assigned. In some implementations, the behavioral insight dashboard may provide a template of psychometric profiles that work well together, compare it to the subjects for a board, and make recommendations for the composition of the board.

In some embodiments, the behavioral insight dashboard may integrate third party information to share with its users. For example, a marketing team could survey customers, see their results, and use the results for a better marketing scheme. This may allow companies to better understand their baseline customer and have a larger reach selling their product or service.

Figure 3:
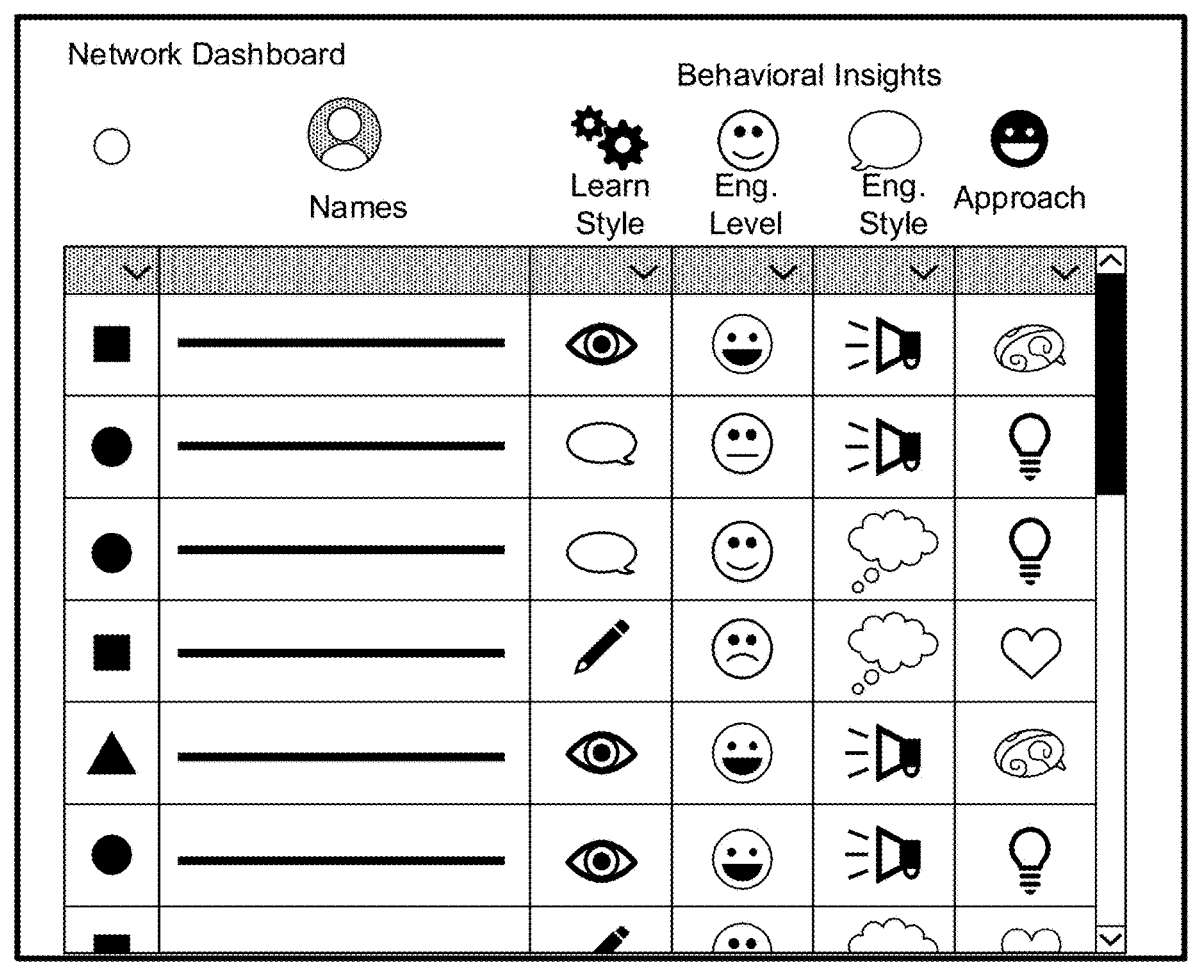

Referring now to FIG. 3, an exemplary team report dashboard is illustrated. In some embodiments, a team report dashboard may present a list of employees within an organization, wherein the list may indicate general information about each employee, such as their name, contact information, salary, position, number of teams that are part of, and how often their profiles have been viewed, as non-limiting examples. The list may include a summary or shorthand references to each employee's psychometric profiles and behavioral insights, such as an archetype label.

In some aspects, a team report dashboard may present available team reports, wherein clicking into each team label may link to each individual team report. In some embodiments, the employee list may indicate which employees have linked their psychometric profiles to the organization. For employees who have not linked their psychometric profiles, the team report dashboard may provide an option to send a request, which may prompt the employee to link their psychometric profile. If the employee has not yet created a psychometric profile, the request may prompt them to create one.

In some embodiments, the company may have the ability to invite different users to the dashboard. In some aspects, the company may choose the level of access each user has, from cursory behavioral insights to full dashboard access. For example, the employer may have full control of the dashboard and give managers significant access to their team and limit base level employees to cursory behavioral insight information. In some aspects, the managers may have access to behavioral insights for each team member and as a team.

In some embodiments, group dashboards may allow for understanding of behavioral insights for select group members within a larger pool. For example, the larger pool may comprise employees, service providers, and clients. The groups may be separated and parsed based on need. For example, a client behavioral insight dashboard may be useful when developing a marketing plan. As another example, employee behavioral insights may be useful when understanding the effectiveness and productivity of the employee pool. Each group may be further segmented and customized based on the particular purpose for understanding.

In some embodiments, the dashboard may be connected to other forms of social media to help employers and employees communicate better even when not on the dashboard at the same time. In some aspects, the dashboard my update when new information comes up on social media. In some implementations, managers and the employer may update the dashboard when they see new information come from connected social media. In some implementations, the dashboard may suggest groups based on interactions on connected social media platforms. For example, two users may interact regularly on social media and the dashboard may recognize this and put them in the same suggested group.

Figure 4A:
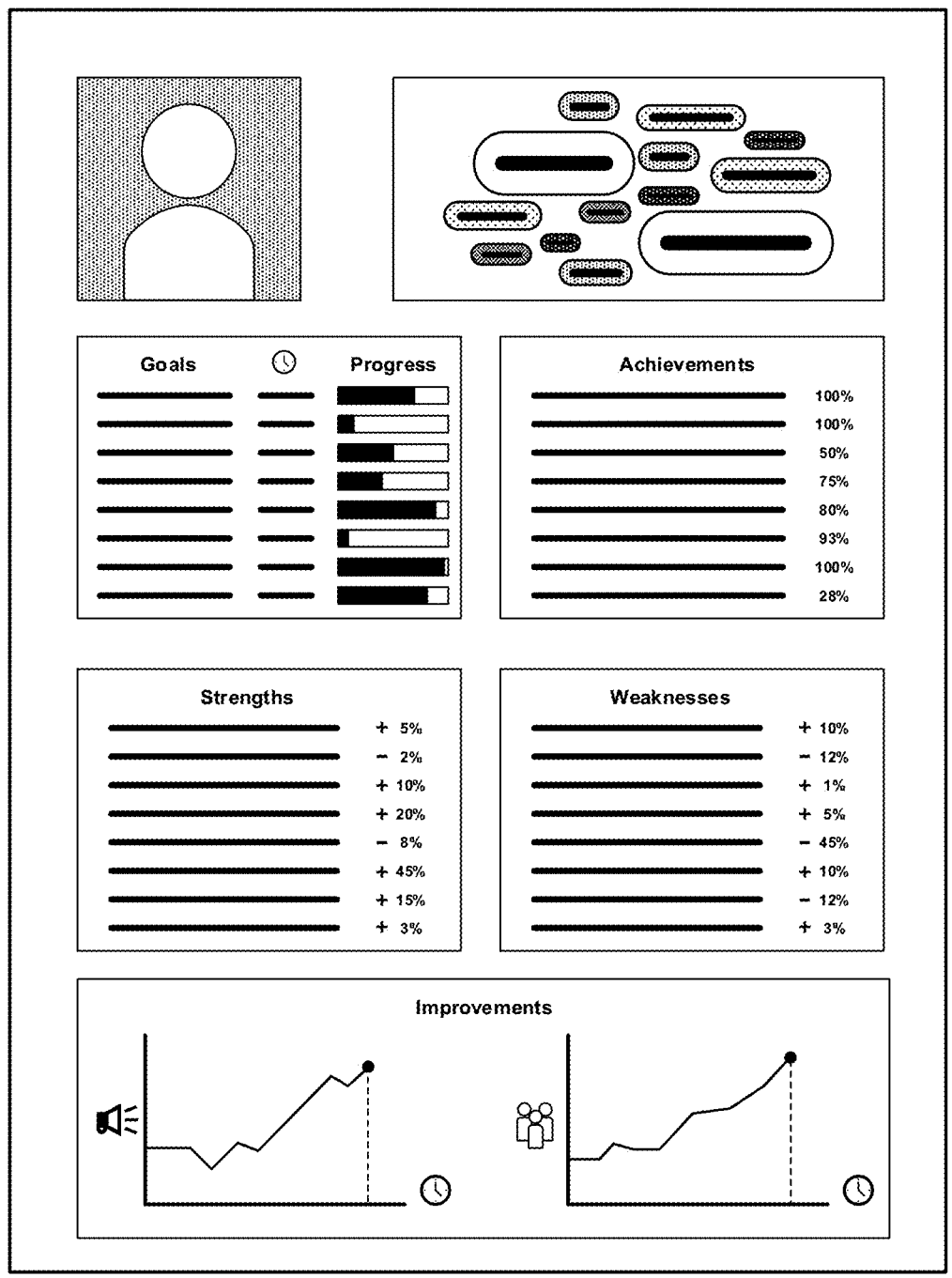
FIG. 4A illustrates an exemplary individual behavioral insight dashboard, according to some embodiments of the present disclosure.

Referring now to FIG. 4A, an exemplary behavioral insight dashboard for an individual is illustrated. In some aspects, behavioral insights may be presented as a combination of graphics, numbers, and text. In some embodiments, the behavioral insights may be presented in context of employment, wherein information is provided for both the individual and for those who may work with the individual.

In some implementations, the behavioral insight dashboard may present success predictions for various roles, such as within different company sizes, company stages, and management positions, as non-limiting examples. In some embodiments, the behavioral insight dashboard may logically interface with third party psychometric assessment platforms, wherein the behavioral insights may be based in part on data associated with the individual from the platforms. In some aspects, the behavioral insight dashboard may incorporate other attributes, such as interests, skills, aspirations, experience, performance data, and feedback data, as non-limiting examples. In some implementations, the behavioral insight dashboard may recommend groups or activities for an individual to join based on the information the individual enters, such as interests, aspirations, skills, behavioral insights, schedule, or combinations thereof.

In some embodiments, the behavioral insight dashboard may make recommendations for an individual to meet based on their psychometric profile. In some implementations, a user may input information about themselves in their profile, such as education or degree, majors or minors from university, employment history, extracurricular activities, interests, or courses they are taking. In some aspects, the system may make recommendations to a user to meet other people based on this extra information. In some embodiments, the system may pair a psychometric profile with additional information to make recommendations to a user.

For example, a user may be a college student who recently started their freshman year. Based on the dormitory they are staying at, their current declared major, and the courses they are taking, the system may recommend a mentor, such as an upperclassman, and potential peers, such as neighbors within their dormitory or close by that have similar career goals. By way of another example, an employee working at a large corporation with 500 or more employees and multiple locations may get a recommendation to speak to someone that is in a department that sometimes interacts with theirs, or with a potential mentor who used to work in their position.

In some aspects, the dashboard may track the evolution of the company's life or the user's life at a company. In some aspects, if the user has worked at more than one company then their life at each company may be tracked and shown on their profile. In some aspects, a company's profile may be accessed to determine if their workforce is stagnant or thriving. In some implementations, a sunburst chart may be used to track the evolution of the company's workforce growth and the overall makeup within the company. Viewing group behavioral insights may allow an employer or manager to not only view productivity, compatibility, and effectiveness, but to understand the potential reasoning behind the results. This may allow for meaningful and effective changes to improve attributes based on behavioral insights, which may be a proactive approach rather than only reactive.

In some embodiments, a behavioral insight dashboard may display engagement of the group, as a whole or by group member. In some embodiments, the company's profile may be integrated with social media and show how many company employees are connected versus how many employees are in the company. In some aspects, the connections may gauge how involved the company's employees are with the company. In some aspects, third parties may click on employees' profiles who are connected and show portions of information of their profile. In some embodiments, third parties may have the option to connect with employees within the company or invite them to join other communities.

In some aspects, the employer may require its employees to spend time learning certain skills before they are allowed to connect. For example, the user may have a pending request to join until they complete a certain number of hours of training in Microsoft Excel. In some implementations, this may show that the company does not have a stagnant workforce when viewing the sunburst chart. In some aspects, the company may require its group pool to do a certain amount of training each quarter, such as based on role or function of each group member to the company.

Figure 4B:
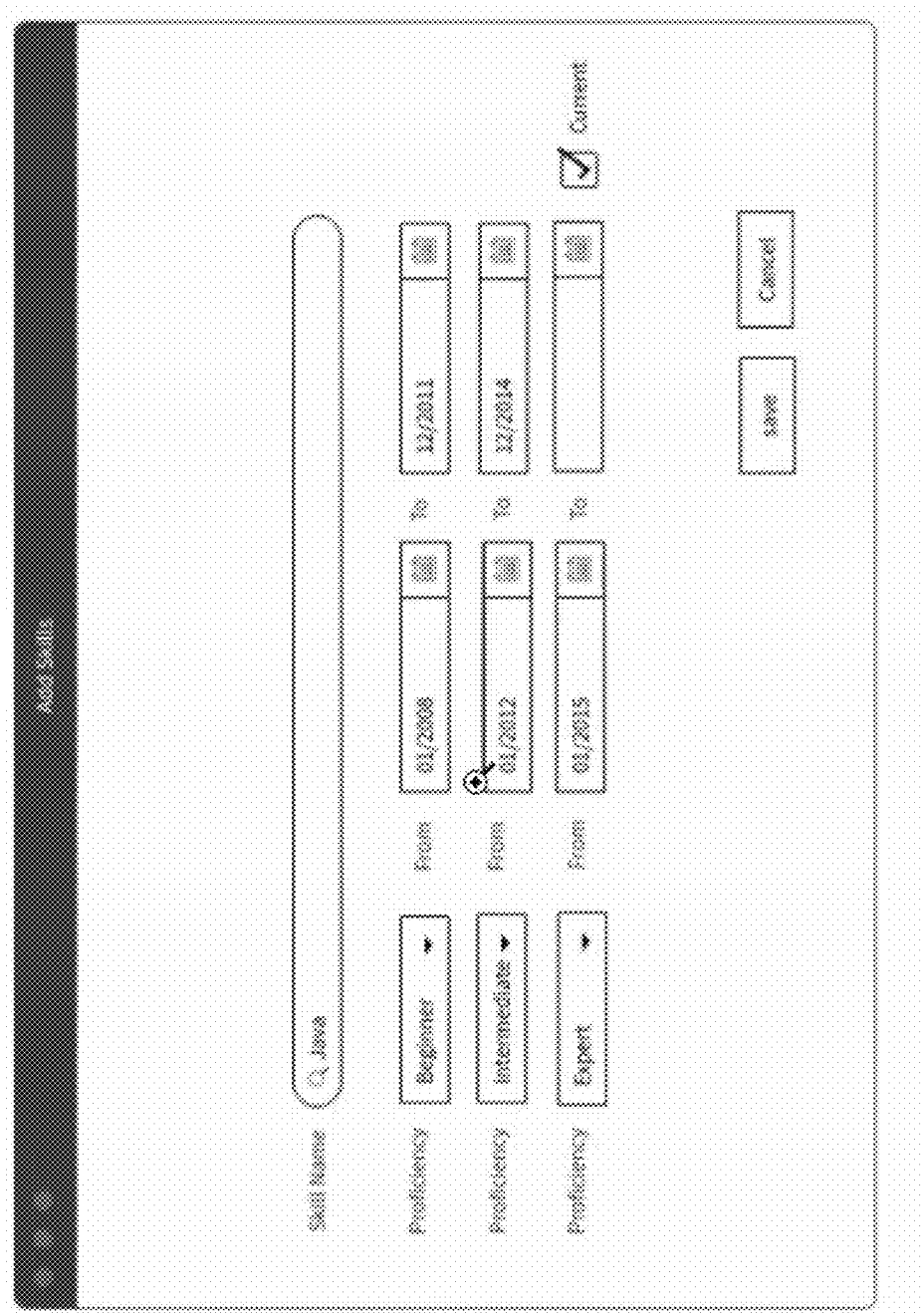
FIG. 4B illustrates exemplary profile data entry, according to some embodiments of the present disclosure.

Referring now to FIG. 4B, exemplary profile data entry is illustrated, wherein a user may be able to view and edit their skills. In some aspects, a user may be part of multiple teams, which may be within the same or different enterprises. As non-limiting examples, a user may be part of teams based on a project, a role, a position, a department, or company. A user may be part of teams within their own company and within other companies, such as service providers, vendors, or customers. In some embodiments, a user may be able to view the behavioral insights for each team they are part of by clicking into the teams.

In some implementations, the dashboard may present some team information for ease of reference, such as team names, number of members, and company name. In some embodiments, a user may be part of professional and personal teams. For example, a user may be a neurosurgeon at a hospital, an expert medical witness for a company, a little league coach and scout master to her daughters, and a volunteer doctor for a local charity. The user dashboard may reflect those team memberships. In some aspects, each team behavioral insights may be viewable by team members, team leaders, or designated people or groups. In some implementations, a user may be able to add other profile details from this dashboard, such as education, experience, language, interests, and aspirations, as non-limiting examples.

In some aspects, a user may receive a rating, which may be based on the user generally or may be more specific, such as by team, company, or other attribute. In some embodiments, the rating may factor in feedback, behavioral insights, psychometric profiles, performance data, input attributes, or combinations thereof, as non-limiting examples.

In some implementations, the user may have full control over all their skills their experience level with those skills.

For example, the user may input a skill, the amount of time they have been practicing, and their estimated level. In some aspects, the user may edit their skill level as they progress with it throughout their educational journey or career. In some aspects, an employer or someone with access to the user profile may endorse the user or raise their skill level at any time. In some embodiments, skills and skill level may require proof of that skill or level, such as through testing or requesting third party confirmations.

In some aspects, the user may indicate how long they have been using this skill and in what circumstances they have used it in. For example, the user may have the ability to put specific dates and companies or uses under then skill. In some aspects, the user may edit these dates and uses at any time if changed. In some implementations, third parties may be able to input skill data, and the system may compare the third-party input to the user input. Where the data aligns, the behavioral insight dashboard may be updated. Where the data conflicts, the system may follow up before updating.

In some embodiments, a user dashboard may provide a visual resume, wherein typical resume information may be illustrated. In some aspects, a visual resume may be animated to show the personal development of the user over time, which may be more enlightening than a static resume, which only captures skills and experience from a specific moment in time. An animated resume may allow the user or someone viewing the dashboard to filter by date, so that only a relevant portion of the resume is visible. For example, a potential employer may only care about the user's professional development starting after college graduation.

Figure 5C:
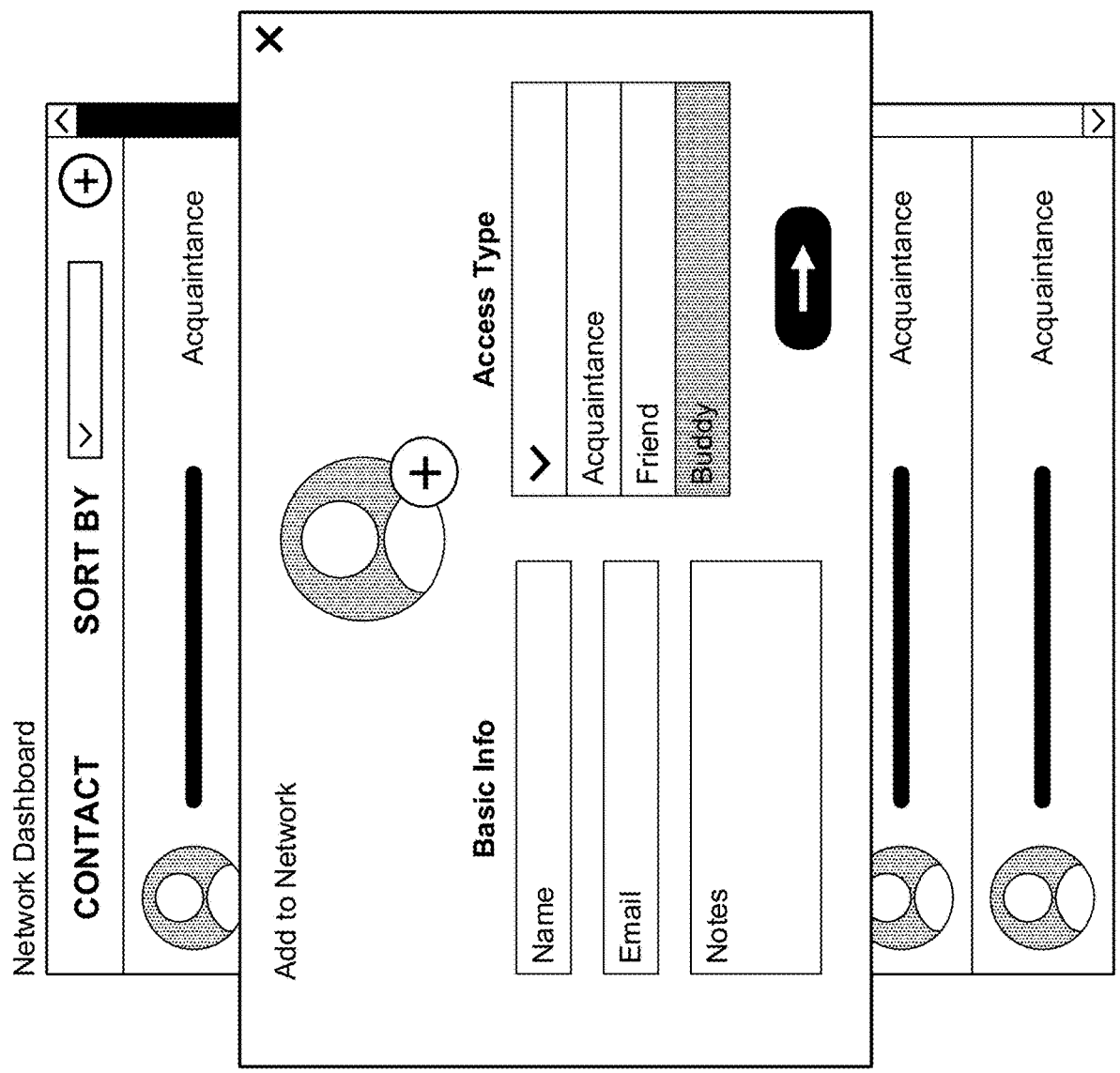
FIG. 5C illustrates an exemplary network addition request, according to some embodiments of the present disclosure.

Referring now to FIGS. 5A-5B, an exemplary network behavioral insight dashboard is illustrated. Referring now to FIG. 5C, an exemplary network addition request is illustrated. In some embodiments, the user may invite people to view their profile and give them access based on their relationship. In some aspects, an acquaintance from a past employer or educational experience may simply be connected to their network and only their approved comments may be attached to the user profile. In some implementations, the user may invite a friend from their company or life, and they can endorse skills, work ethic and other profile data. In some embodiments, a boss or family member may have the most access to the user profile and may adjust things like qualifications, behavioral data, and personality traits.

In some implementations, the user profile may be connected to social media platforms and they can use this to connect with their invitees. For example, the user may invite all their connections from their social media connections and give each one unique access based on how well they know that connection. In some aspects, the user may always override an adjustment or edit on their profile despite the access of their invitee. In some implementations, the user may raise or lower one's access to their profile at any given time.

In some aspects, the user may connect the contacts from their phone or smart device in the event that one of their connections does not have a social media account. In some embodiments, the dashboard may recommend the user to join groups or communities within the system based on their connections, hashtags, user data, or other forms of patterns the system recognizes. For example, a user may be asked to join a specific community based on what company they work for, that way their employer may access to their user profile to use and update throughout their work career.

In some aspects, each community may indicate what common groups or companies each member is a part of. For example, if two user profiles are not connected but in a similar group, each user may be notified and be given the option to connect with one another. In some aspects, the user profile may give third parties access to their connections and all information regarding them. For example, a third party may be able to see the level of access, common communities, and how long two user profiles have been connected when they click on a user profile.

Figure 6:
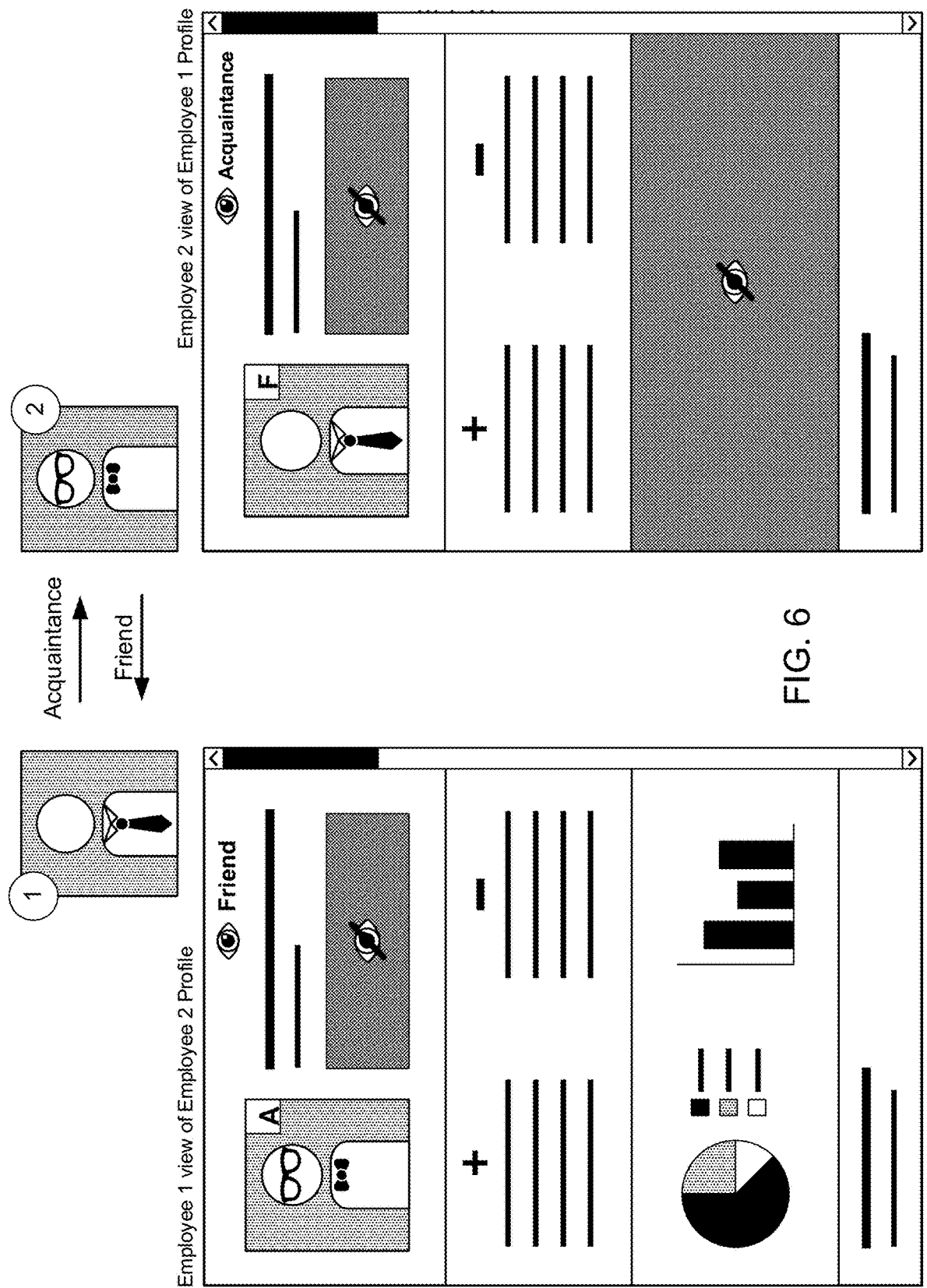
FIG. 6 illustrates profile visibility between users within a shared network, wherein visibility is based on access level.

Referring now to FIG. 6, profile visibility between users within a shared network is illustrated, wherein visibility is based on access level. In some embodiments, subjects may want to connect with each other, wherein each subject shares at least a portion of their behavioral insight dashboard with each other. In some aspects, each subject may independently control access, wherein the subjects may permit different access to the other subject.

As an illustrative example, subject 1 may connect with subject 2 as an acquaintance, and subject 2 may connect with subject 1 as a friend. The system may analyze each subject's dashboard, assigning visibility values to each segment, such as name segment, skill segment, general behavioral insight segment, detailed behavioral insight segment, and feedback segment, as non-limiting examples. The visibility values may determine privacy levels, and each subject may request a connection with a threshold visibility value, wherein any segments valued less than the threshold visibility value are visible to the connecting subject.

In some aspects, behavioral insight dashboards may vary between subjects, and each behavioral insight dashboard may be segmented and valued separately. In some embodiments, behavioral insight segments may be presented differently to different subjects based on each subject's behavioral insights. For example, a general behavioral insight segment that indicates a subject comprehension style may look different to subject 1 and subject 2. Subject 1 may benefit from detailed textual descriptions whereas subject 2 may prefer illustrations, and visibility of subject 1's behavioral insight dashboard segment may be customized to both needs.

In some embodiments, a user may submit a request to view another profile, wherein that request may specify a level of access. For example, a potential employer may request full access to a user's profile. In some aspects, group profiles may be limited to partial visibility for all users, wherein only users who control the dashboard are able to view the entire profile. This may be useful for team or company dashboards that may contain private individual information that would be inappropriate to share. The highest shared access may comprise group profile data that may not specifically identify any particular team member.

In some aspects, a user may be presented with suggested connections, such as based on associations, other connections, group memberships, and behavioral insights, as non-limiting examples. In some embodiments, a user or team administrator may customize how suggestions are made, wherein the user may identify criteria that may prompt suggestions. As an illustrative example, a user may only allow for suggestions based on class schedule and professor, which may allow the user to collaborate with other students taking the same classes.

As another illustrative example, a team administrator may want to prompt meaningful connections between team members, particularly those who would not typically interact. Team members may be suggested based on behavioral insights and team membership. Team members who may operate within different sub-teams, team members with similar skills, insights, talents, and aspirations, or team members with different or even opposing behavioral insights may benefit from connecting, which may increase engagement and inter-personal development for team members.

Referring now to FIG. 7, an exemplary team behavioral insight dashboard is illustrated. In some aspects, the aggregated psychometric profiles and behavioral insights may be provided for a team. In some embodiments, a team may be manually selected or may be based on identified groups, such as by project, department, position, location, or performance types, as non-limiting examples.

In some implementations, it may be useful to view the overall makeup of a team to understand how they can be successful. For example, knowing that a team is lacking any member with an attention to detail may prompt the company to add a detail-oriented person to the team who may also complement the other team attributes. As another example, knowing that a team is competitive in a productive manner may inform how projects are presented to them so as to encourage their competitive nature.

In some aspects, as team members may be added and removed, the aggregate behavioral insights may change to reflect the removed or added psychometric profiles. In some embodiments, this may occur in real time. This may allow for immediate behavioral insights based on adjustments to team dynamics. A team builder may utilize this feature to tailor a team to a specific goal. In some aspects, a team builder may utilize this feature to adjust a team to be more effective.

In some embodiments, the system may suggest ways to improve a team or may suggest team memberships. For example, based on behavioral insights, the system may suggest team building exercises that may increase camaraderie for one team, and the system may suggest adding in a detail-oriented member to a team that lacks that attribute. In some aspects, behavioral insights may allow a company to develop an effective team for a specific client, for a specific task, for a specific department, or for a specific role, as non-limiting examples.

In some aspects, the system may give the team suggestions on what member would be best in what spot of the team. In some implementations, the system may recommend changes to balance the psychometric profiles of the subjects in a given team. For example, a team member may be more useful as a marketing director rather than a treasurer, and the system may be automated to tell the team leader or members. In some aspects, the system may recommend changes to the team based on balance assessments, wherein the behavioral insights as a whole are analyzed to determine how well balanced they are. For example, if a team comprises only members who comprehend through understanding the big picture, the system may suggest a detail-oriented member to balance the behavioral insights, which may allow the team to operate more effectively.

In some embodiments, the system may provide a template for a team based on individual, company, or collective need. In some aspects, the system may rank subjects for who might be best suited for a team. In some implementations, the system may identify what psychometric profiles may work best together. In some embodiments, the system may provide suggestions to team members on how to work most effectively with one another. In some implementations, the system may integrate team feedback on whether a team member needs to be replaced.

In some aspects, as members are added to a team, the system may show the cumulative psychometric profile based on who is placed in the team. In some embodiments, the system may generate the cumulative psychometric profile visually where a user can click in and see the breakdown of how that profile was generated based on who is in the team. In some implementations, the system may make recommendations in real-time based on who is added to the team. In some aspects, the system may integrate the team's purpose into how the system makes a recommendation. For example, if the purpose of the team is for a school science project, the composition might be entirely different when compared to a school art project. To that end, the system's recommendations may be entirely different when determining who might be a good fit for a company board or when determining who needs to be on a marketing team.

In some embodiments, such as where students have limited control over their scheduling, students may be assigned professors and schedules that suit their psychometric profile. In some implementations, the assignment may be based on professor curriculums, professor psychometric profiles, behavioral insights on student's learning and studying styles, student associations, student interests, student networks, or combinations thereof as non-limiting examples. In some aspects, where students may have complete control of their schedules, such as with upperclassmen, the system may suggest an effective schedule, such as based on selected courses, selected major, courses already taken, associations, interests, networks, behavioral insights, or combinations thereof, as non-limiting examples.

In some implementations, psychometric profiles may allow for effective pairing in clubs, such as debate teams. Understanding the psychometric profiles of each team member may allow each student to debate against a range of personality and debate types, which would better prepare them for a debate. In some aspects, an opponent may be unknown so preparing against a range of personalities would be effective, and in some embodiments, an opponent may be known or may be selected from a known group. The debate team may have access to the psychometric profiles of their opponents and prepare accordingly.

Figure 8A:
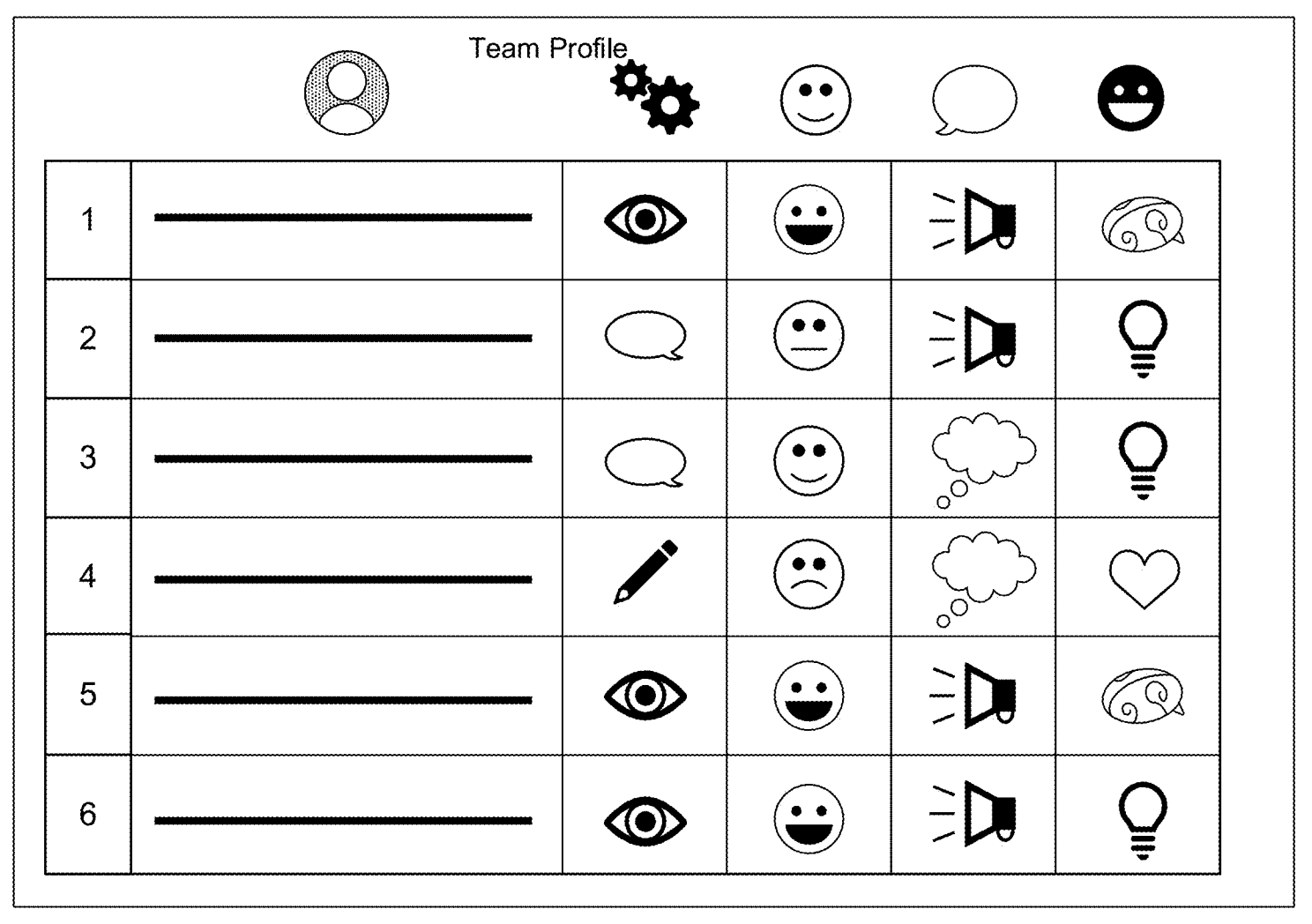

Referring now to FIG. 8A, an exemplary team composition dashboard is illustrated. In some aspects, a team may be constructed through a cloning process, wherein the team composition characteristics for the team may be manually set. In some embodiments, the candidate pool for the team may be defined, such as any employee of the organization, any person not in a management role, or any person in a specific department or position, as non-limiting examples. In some embodiments, a team composition dashboard may provide a compatibility analysis, which may indicate how well a team may work together. In some aspects, a team composition dashboard may indicate how balanced a team is, where opposing behavioral insights may create a balanced team. For example, a team with only risk averse members may be too conservative, and a team with only risk takers may create solutions that are too risky. A balanced team may have both risk takers and risk averse members.

The behavioral insights for each member may guide how to effectively balance the team. For example, if the team comprises five moderate risk takers, then a single team member that is very risk averse may balance the team. If the team comprises three extreme risk takers, then it may require a mix of moderate and extreme risk averse members to balance the team.

In some implementations, once the team composition characteristics are set, the system may generate team composition options from the candidate pool. In some aspects, various teams may be generated based on the team composition characteristics, wherein the aggregated psychometric profiles of the teams may be similar to the team composition characteristics. In some embodiments, the teams may comprise defined archetypes, such as an engager, alpha, community builder, or other classification, wherein the team options provide different combinations of those archetypes to achieve similar aggregated psychometric profiles.

In some implementations, the various teams may comprise specific individuals whose aggregated psychometric profiles may be similar to the team composition characteristics. In some aspects, a user may be prompted to select a team archetype makeup, which may then prompt generation of teams of identified individuals. In some implementations, the team composition characteristics may be populated based on known successes, such as the founders of a specific startup, or success trends, such as typical psychometric makeup of successful startups.

Referring now to FIGS. 8A-8B, exemplary behavioral insights for a team are illustrated, wherein the behavioral insights are based at least in part on psychometric profiles. In some embodiments, a team may comprise an organizational team, such as within a particular department or assigned to a particular project. In some aspects, a team may comprise an invitee list for a meeting, as the invitees may be considered a specialty team assigned to the goal or purpose of the meeting.

In some implementations, a team may comprise the founders of a company or the c-suite of a company. In some aspects, a team may be an existing team or one that has not yet been built. Understanding the aggregate behavioral insights and psychometric profiles of a team may allow for a better understanding on how to help the team succeed. It may be helpful to anticipate the strengths and weaknesses of a team before it is created. In some aspects, the team may be adjusted to create a more balanced or effective aggregate psychometric profile.

For example, a venture capital group may be interested in investing in a startup with three founders. An understanding of their behavioral insights and psychometric profiles, both aggregated and individual, may allow them to make a more informed decision. They may also use the information to add or remove team members to increase the chance of success of the startup. In some embodiments, there may be known psychometric profiles or identified successful teams for particular goals, such as founders of a successful startup, wherein a comparison of a team's psychometric profiles and behavioral insights may be useful to predict outcomes.

In some aspects, a team may periodically or regularly update their results. In some embodiments, the system may identify reoccurring problems not previously stated or recorded and update its recommendations accordingly. By way of example, the system may have put students together to work on a school project. Over time it may become clear that a team member may not be working as hard. The system may then suggest different ways for that member to be more efficient or to have a more enjoyable time.

Figure 9A:
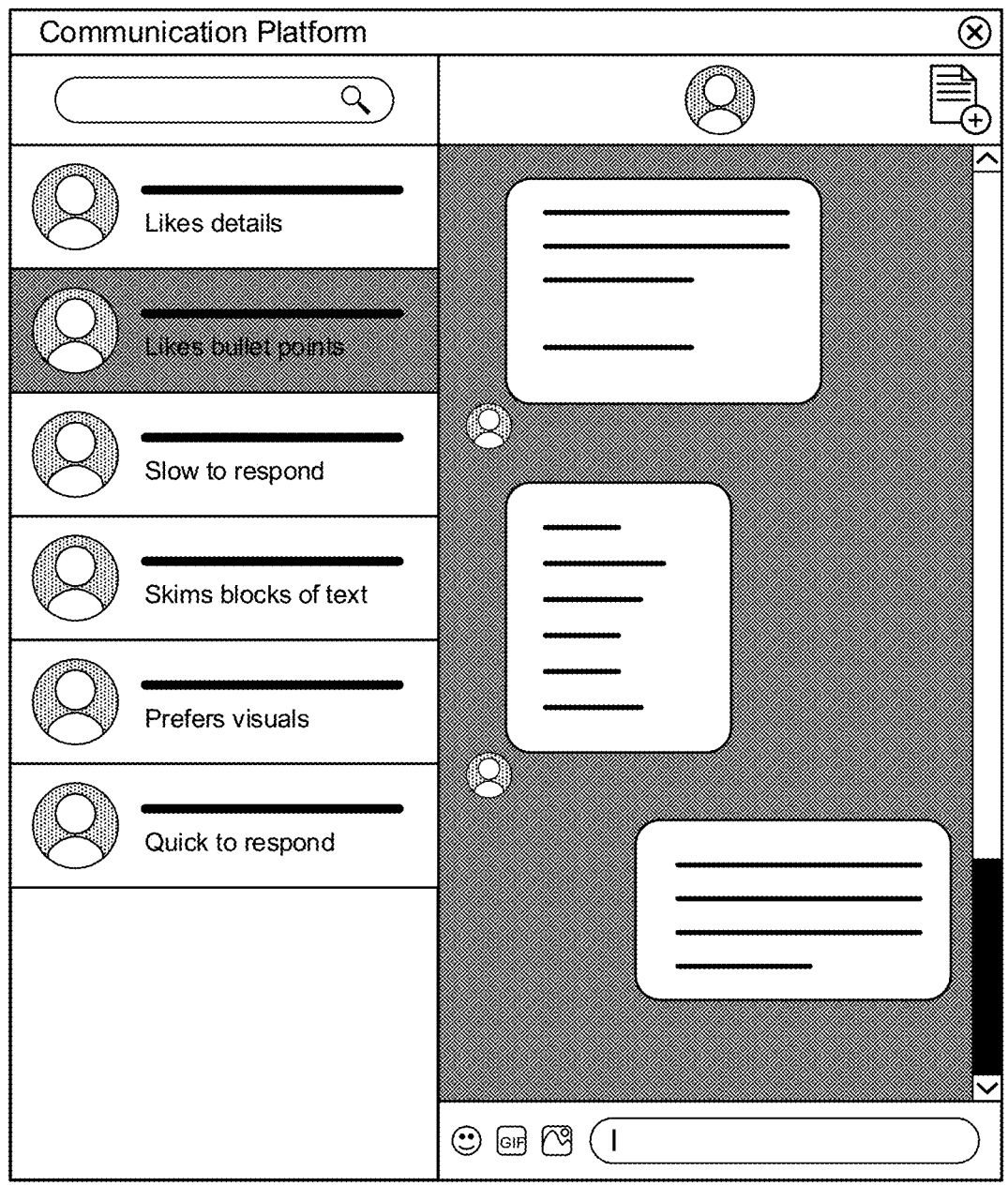
FIG. 9A illustrates an exemplary integration of behavioral insights with a communication platform.
Figure 9B:
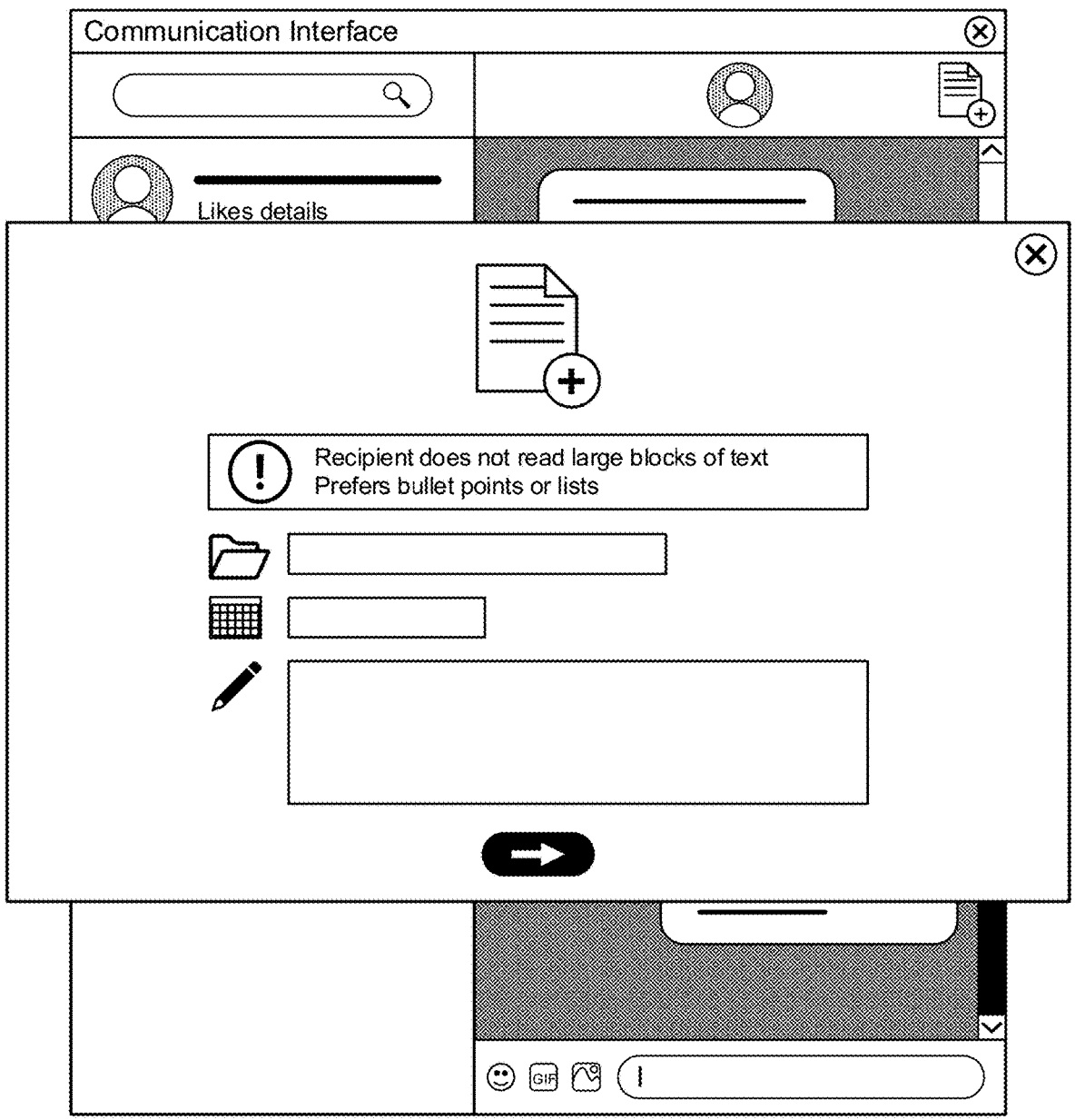
FIG. 9B illustrates an exemplary integration of behavioral insights with a communication platform.

Referring now to FIGS. 9A-9B, an exemplary integration of behavioral insights with an external communication platform is illustrated. In some embodiments, an external communication platform may allow for direct communication between individuals, groups, and individuals and groups. In some aspects, the direct communication occurs through chat boxes and instant messaging. In some implementations, subject behavioral insights may be provided in real time as an individual is typing a message to a subject. In some embodiments, behavioral insights may be provided for multiple subjects in a side tab. The behavioral insights may be provided on an individual subject basis where separate behavioral insights are provided with each subject. In some aspects, group behavioral insights may be provided, such as in a group chat or for a team of individuals.

Real time display of behavioral insights may allow for more effective and efficient communication. For example, if a subject is "slow to respond", the person communicating with that subject may have more realistic expectations, wherein the person may be more tolerant of a slow response. As another example, if a subject prefers bullet points, the person communicating with that subject may present communication through bullet points. Being able to refer to individual behavioral insights may allow for individualized communication.

In some embodiments, a method of providing behavioral insights may comprise customizing communication based on individual behavioral insights. For example, an individual may select three subject recipients, each with different communication and comprehension styles. The individual may input a universal message for the team, and the system may customize the communication to fit the individual needs of each subject. The communication may be translated into bullet points for one subject, illustrative visuals for another subject, and remain detailed for a last subject. Where the communication is insufficiently detailed, the system may prompt the person constructing the message to provide more details.

In some aspects, a communication platform may allow a user to send files, meeting invitations, and notes. For any pop-up communication, the system may provide notices or warnings about the subject so that the person communicating is reminded of the behavioral insights associated with that subject. This may limit transmission of ineffective communication and documents. This may also allow for management to track and monitor effectiveness of communication within a group or team. For example, if an individual repeatedly ignores behavioral insights for subject recipients, a manager may be able to address that issue with the individual.

In some embodiments, the system may compare communications with notified behavioral insights, wherein the system may assess whether an individual communicating with other subjects is effectively tailoring their communications based on provided behavioral insights. In some aspects, this may allow for automated review of effective communication without requiring a manual investigation into each communication, which may be limiting for large groups. For example, an enterprise may be able to view communication effectiveness throughout their entire employee pool, and the enterprise may be able to assess whether communication courses or meetings may be necessary to increase effectiveness throughout the enterprise.

Figure 10:
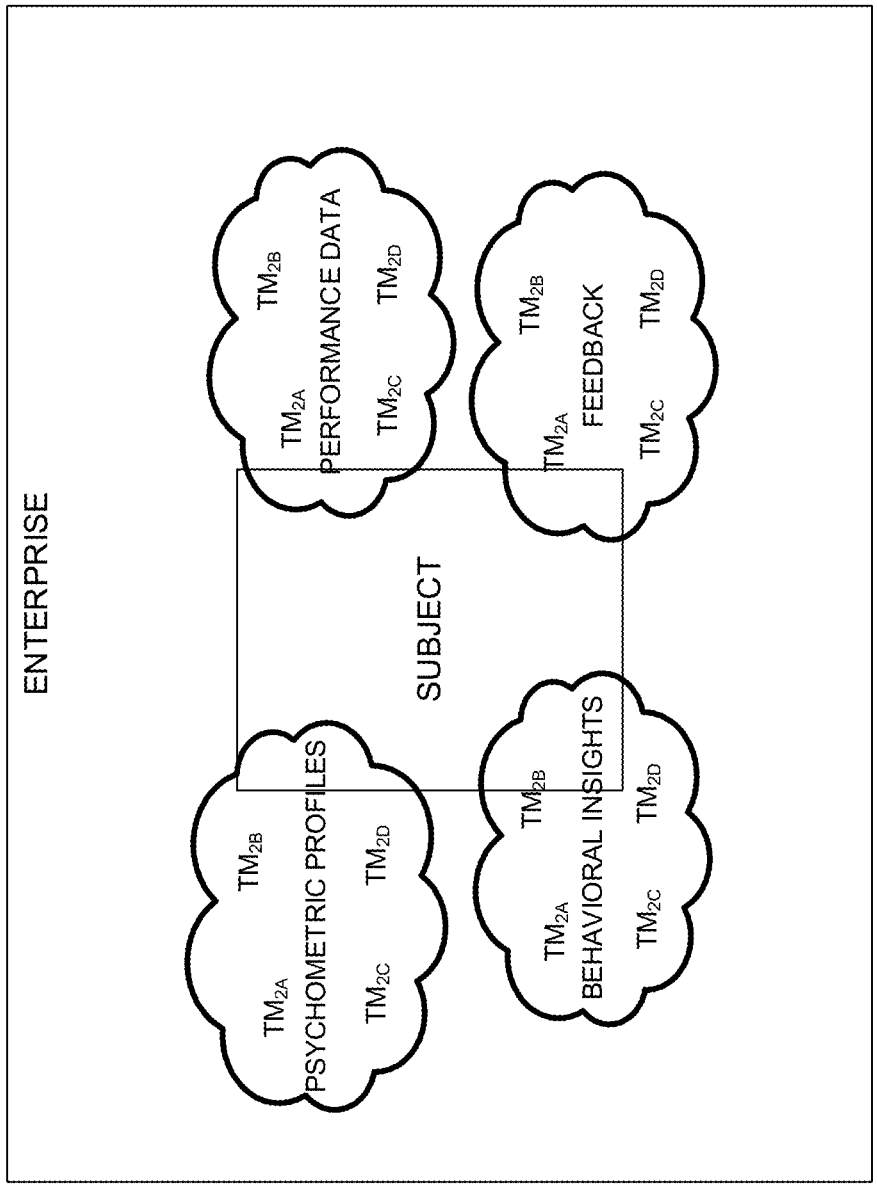
FIG. 10 illustrates exemplary distribution of behavioral insights within an organization, according to some embodiments of the present disclosure.

Referring now to FIG. 10, exemplary distribution of behavioral insights within an organization is illustrated. In some embodiments, an organization may maintain databases with psychometric profiles, performance data, behavioral insights, and feedback. In some aspects, these databases may be maintained in groups or separately. In some implementations, the databases may be organized or categorized by subject, such as by person, team, or position, as non-limiting examples. In some aspects, the databases may be logically linked, which may allow for correlation between the data, such as by subject.

For example, the subject may comprise an individual, and her psychometric profile and behavioral insights may be compared to her performance and feedback. This may allow for an assessment of whether she is performing above or below expectations based on her behavioral insights. In some aspects, her performance may be compared to her feedback, which may provide insight as to how effective the feedback has been and whether her responses have been in line with expectations or predictions based on her psychometric profile and behavioral insight.

In some embodiments, the system may correlate behavioral patterns and highlight behavioral patterns per each individual. This may help the individual manage unknown behavioral patterns or may help the employer identify otherwise unnoticeable behaviors by employees. These behaviors may include purposeful behaviors, such as, small mathematical errors, scheduling patterns, or being late.

Figure 11:
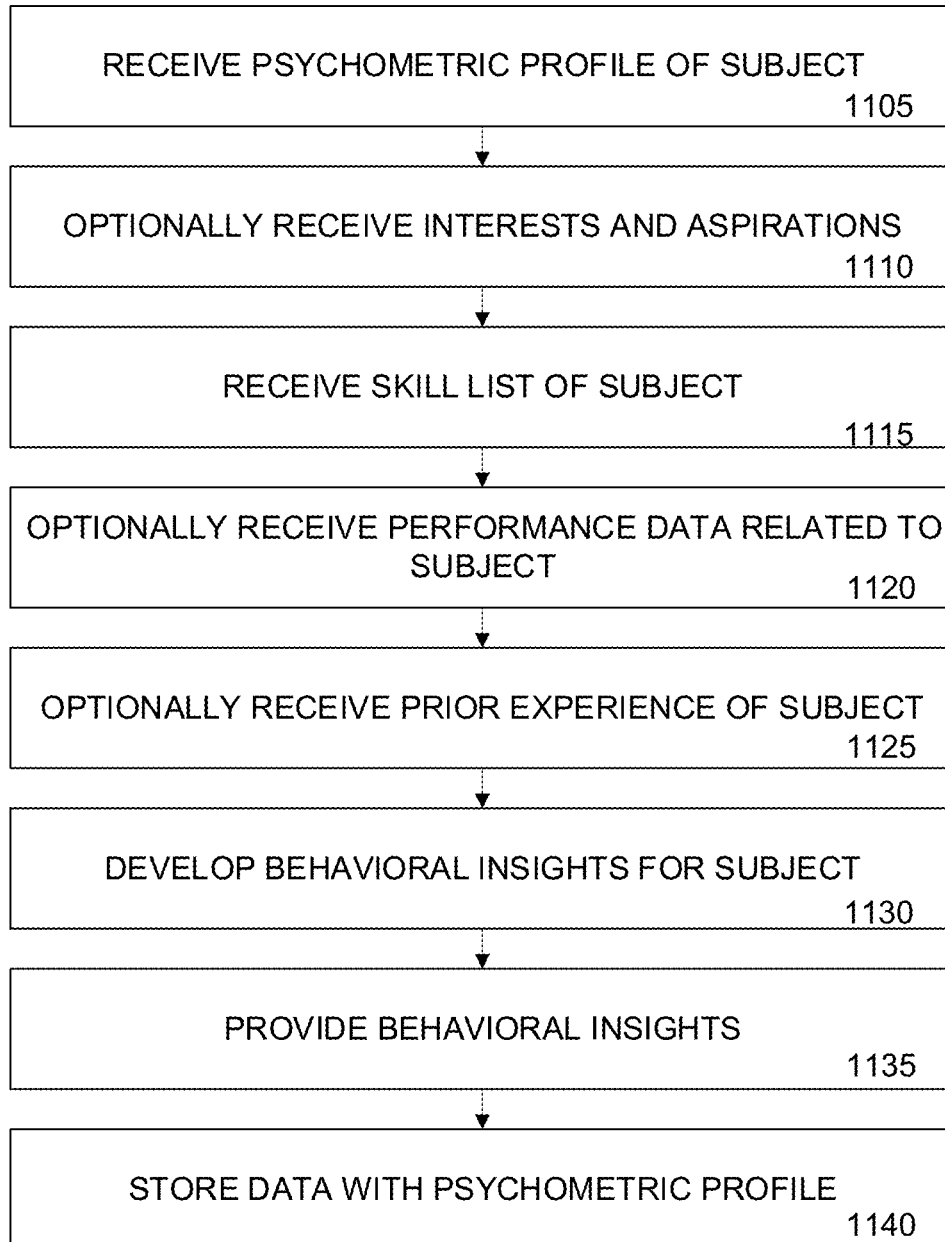
FIG. 11 illustrates exemplary method steps for developing behavioral insights, according to some embodiments of the present disclosure.

Referring now to FIG. 11, exemplary method steps for developing behavioral insights are illustrated. At 1105, a psychometric profile of a subject may be received. In some aspects, at 1110, interests and aspirations of the subject may be received. In some implementations, at 1115, a skill list of the subject may be received.

In some embodiments, at 1120, performance data related to a subject may be received. In some implementations, at 1125, prior experience of the subject may be received. At 1130, behavioral insights of the subject may be developed. At 1135, behavioral insights may be provided, such as to the subject, a manager, or employers, as non-limiting examples. At 1140, the collected data may be stored with psychometric profile.

Figure 12:
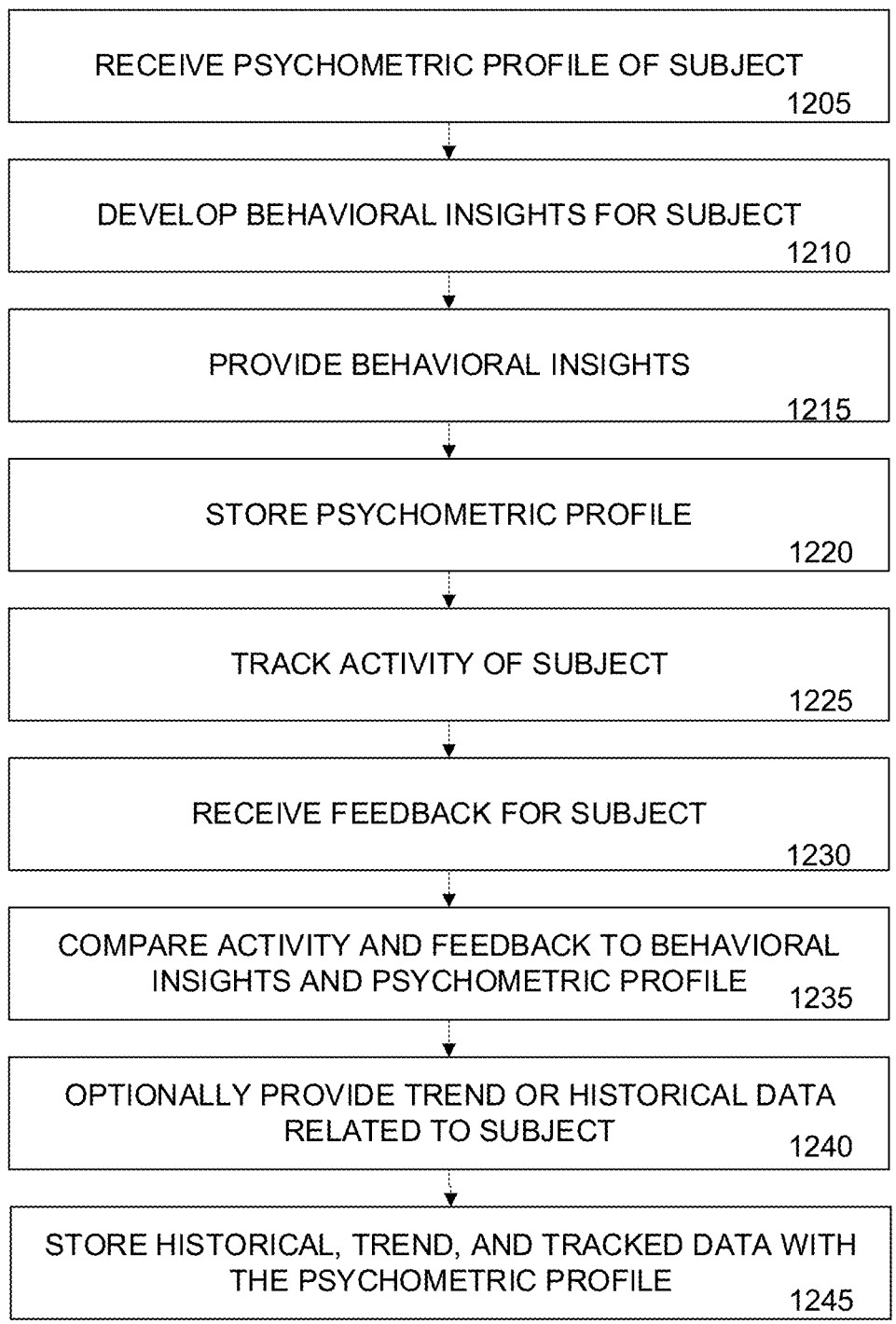
FIG. 12 illustrates exemplary method steps for tracking performance in context of behavioral insights, according to some embodiments of the present disclosure.

Referring now to FIG. 12, exemplary method steps for tracking performance in context of behavioral insights are illustrated. At 1205, a psychometric profile of a subject may be received. At 1210, behavioral insights of the subject may be developed. At 1215, behavioral insights may be provided, such as through a dashboard.

At 1220, the activity of the subject may be tracked. In some aspects, at 1225, feedback for the subject may be received. At 1230, the activity and feedback may be compared to the behavioral insights and psychometric profile. In some embodiments, at 1235, trend and historical data related to the subject may be provided. At 1240, historical, trend, and tracked data related to the subject may be stored with the psychometric profile.

Figure 13:
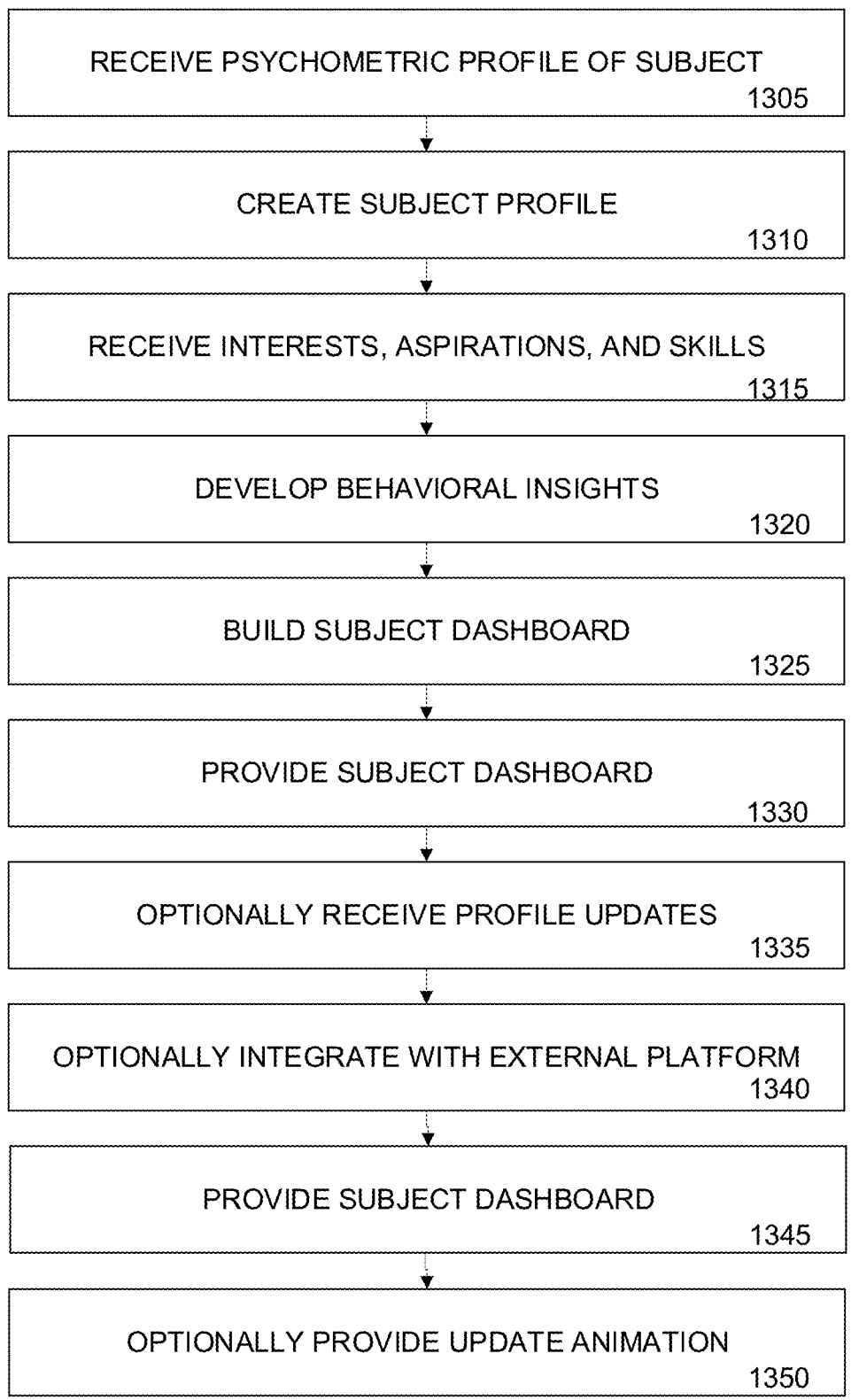
FIG. 13 illustrates exemplary method steps for generating a subject profile.

Referring now to FIG. 13, exemplary method steps for generating a subject profile are illustrated, wherein the subject profile may be for an individual or group. At 1305, one or more psychometric profiles of the subject may be received. At 1310, a subject profile may be created. At 1315, one or more interest, aspirations, and skills may be received. At 1320, behavioral insights may be developed. At 1325, subject dashboard may be built. At 1330, subject dashboard may be provided. In some aspects, 1335, profile updates may be received. For example, updated skill lists, updated interest lists, and updated aspirations may prompt a profile update.

In some embodiments, at 1340, an external platform may be integrated, such as a communication platform, social media platform, or productivity platforms, as non-limiting examples. At 1345, the subject dashboard may be provided. In some implementations, update animation may be provided, wherein the update animation shows a visualization of progress from original profile information to updated profile information. For example, an update animation may show progression of skills over time.

Figure 14:
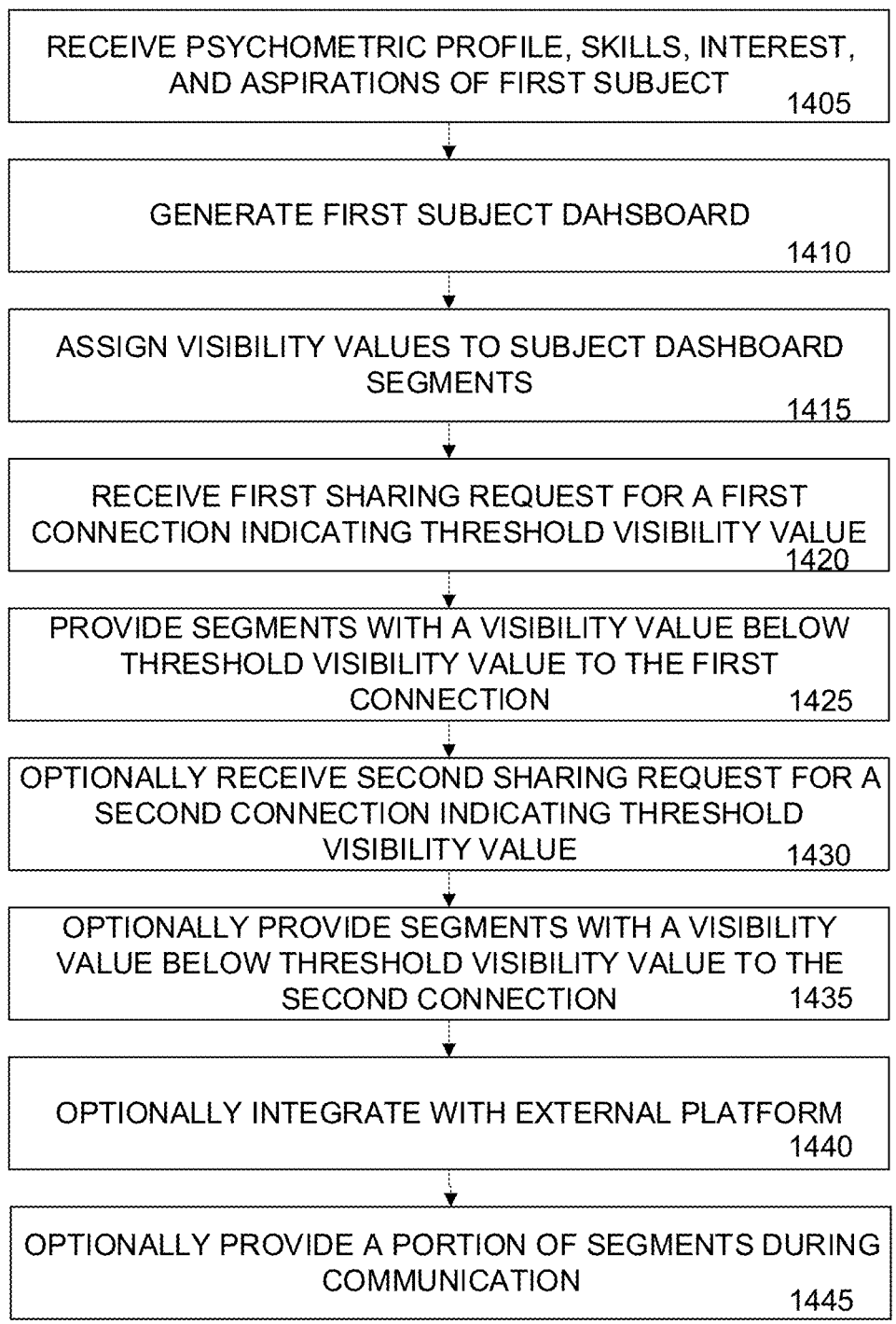
FIG. 14 illustrates exemplary method steps for sharing behavioral insight dashboards based on visibility values.

Referring now to FIG. 14, exemplary method steps for sharing behavioral insight dashboards based on visibility values are illustrated. At 1405, psychometric profile, skills, interests, and aspirations of a first subject are received. At 1410, a first subject dashboard may be generated, wherein the first subject dashboard comprises segments. At 1415, visibility values may be assigned to the segment, wherein the visibility values indicate a privacy level, such as described and illustrated in FIGS. 5A-6. At 1420, a first sharing request for a first connection may be received, wherein the first sharing request indicates a threshold visibility value. In some aspects, the first sharing request may be received from the first subject when inviting a first connection to view their profile. In some embodiments, the first sharing request may be received from the first connection wanting access the first subject dashboard.

At 1425, segments with a visibility value lower than the threshold visibility may be provided to a first connection. In some aspects, at 1430, a second sharing request for a second connection may be received, wherein the second sharing request may indicate a threshold visibility value. In some embodiments, at 1435, segments with a visibility value below the threshold value may be provided to a second connection. In some implementations, the second sharing request may be to access a different subject profile, such as the first connection or the original subject.

In some aspects, visibility values may rank each segment based on privacy levels. Visibility values may comprise color coding, numerical values, illustrations, as non-limiting examples. For example, name, employer, and membership may comprise a low visibility value, as that information may require the least privacy. In contrast, detailed behavioral insights and aspirations may comprise high visibility values that may only be shared with close connections.

In some embodiments, at 1440, an external platform may be integrated, such as a communication platform, social media platform, or productivity platform, as non-limiting examples. In some aspects, at 1445, a portion of the provided segments may be displayed when communicating between the subject and the first connection. For example, as a connection is communicating through an instant messaging platform, behavioral insights of the subject may be provided, wherein the behavioral insights may be limited to information within segments below the threshold value.

Figure 15:
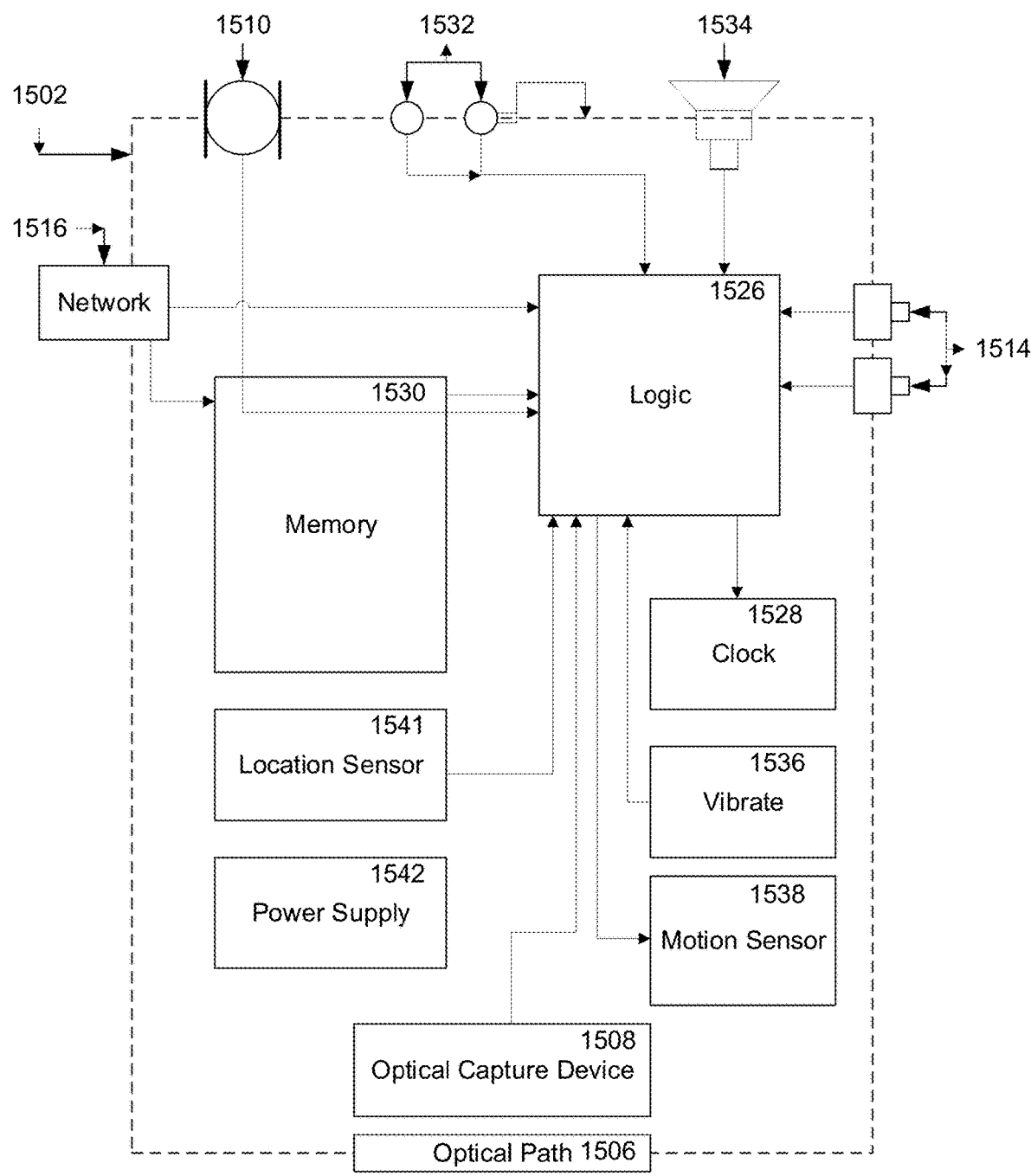
FIG. 15 illustrates an exemplary block diagram of an exemplary embodiment of a mobile device.

Referring now to FIG. 15, an exemplary block diagram of an exemplary embodiment of a mobile device 1502 is illustrated. The mobile device 1502 may comprise an optical capture device 1508, which may capture an image and convert it to machine-compatible data, and an optical path 1506, typically a lens, an aperture, or an image conduit to convey the image from the rendered document to the optical capture device 1508. The optical capture device 1508 may incorporate a Charge-Coupled Device (CCD), a Complementary Metal Oxide Semiconductor (CMOS) imaging device, or an optical sensor of another type.

In some embodiments, the mobile device 1502 may comprise a microphone 1510, wherein the microphone 1510 and associated circuitry may convert the sound of the environment, including spoken words, into machine-compatible signals. Input facilities 1514 may exist in the form of buttons, scroll-wheels, or other tactile sensors such as touchpads. In some embodiments, input facilities 1514 may include a touchscreen display. Visual feedback 1532 to the user may occur through a visual display, touchscreen display, or indicator lights. Audible feedback 1534 may be transmitted through a loudspeaker or other audio transducer. Tactile feedback may be provided through a vibration module 1536.

In some aspects, the mobile device 1502 may comprise a motion sensor 1538, wherein the motion sensor 1538 and associated circuitry may convert the motion of the mobile device 1502 into machine-compatible signals. For example, the motion sensor 1538 may comprise an accelerometer, which may be used to sense measurable physical acceleration, orientation, vibration, and other movements. In some embodiments, the motion sensor 1538 may comprise a gyroscope or other device to sense different motions.

In some implementations, the mobile device 1502 may comprise a location sensor 1540, wherein the location sensor 1540 and associated circuitry may be used to determine the location of the device. The location sensor 1540 may detect Global Position System (GPS) radio signals from satellites or may also use assisted GPS where the mobile device may use a cellular network to decrease the time necessary to determine location. In some embodiments, the location sensor 1540 may use radio waves to determine the distance from known radio sources such as cellular towers to determine the location of the mobile device 1502. In some embodiments these radio signals may be used in addition to and/or in conjunction with GPS.

In some aspects, the mobile device 1502 may comprise a logic module 1526, which may place the components of the mobile device 1502 into electrical and logical communication. The electrical and logical communication may allow the components to interact. Accordingly, in some embodiments, the received signals from the components may be processed into different formats and/or interpretations to allow for the logical communication. The logic module 1526 may be operable to read and write data and program instructions stored in associated storage 1530, such as RAM, ROM, flash, or other suitable memory. In some aspects, the logic module 1526 may read a time signal from the clock unit 1528. In some embodiments, the mobile device 1502 may comprise an on-board power supply 1542. In some embodiments, the mobile device 1502 may be powered from a tethered connection to another device, such as a Universal Serial Bus (USB) connection.

In some implementations, the mobile device 1502 may comprise a network interface 1516, which may allow the mobile device 1502 to communicate and/or receive data to a network and/or an associated computing device. The network interface 1516 may provide two-way data communication. For example, the network interface 1516 may operate according to an internet protocol. As another example, the network interface 1516 may comprise a local area network (LAN) card, which may allow a data communication connection to a compatible LAN. As another example, the network interface 1516 may comprise a cellular antenna and associated circuitry, which may allow the mobile device to communicate over standard wireless data communication networks. In some implementations, the network interface 1516 may comprise a Universal Serial Bus (USB) to supply power or transmit data. In some embodiments, other wireless links known to those skilled in the art may also be implemented.

Figure 16:
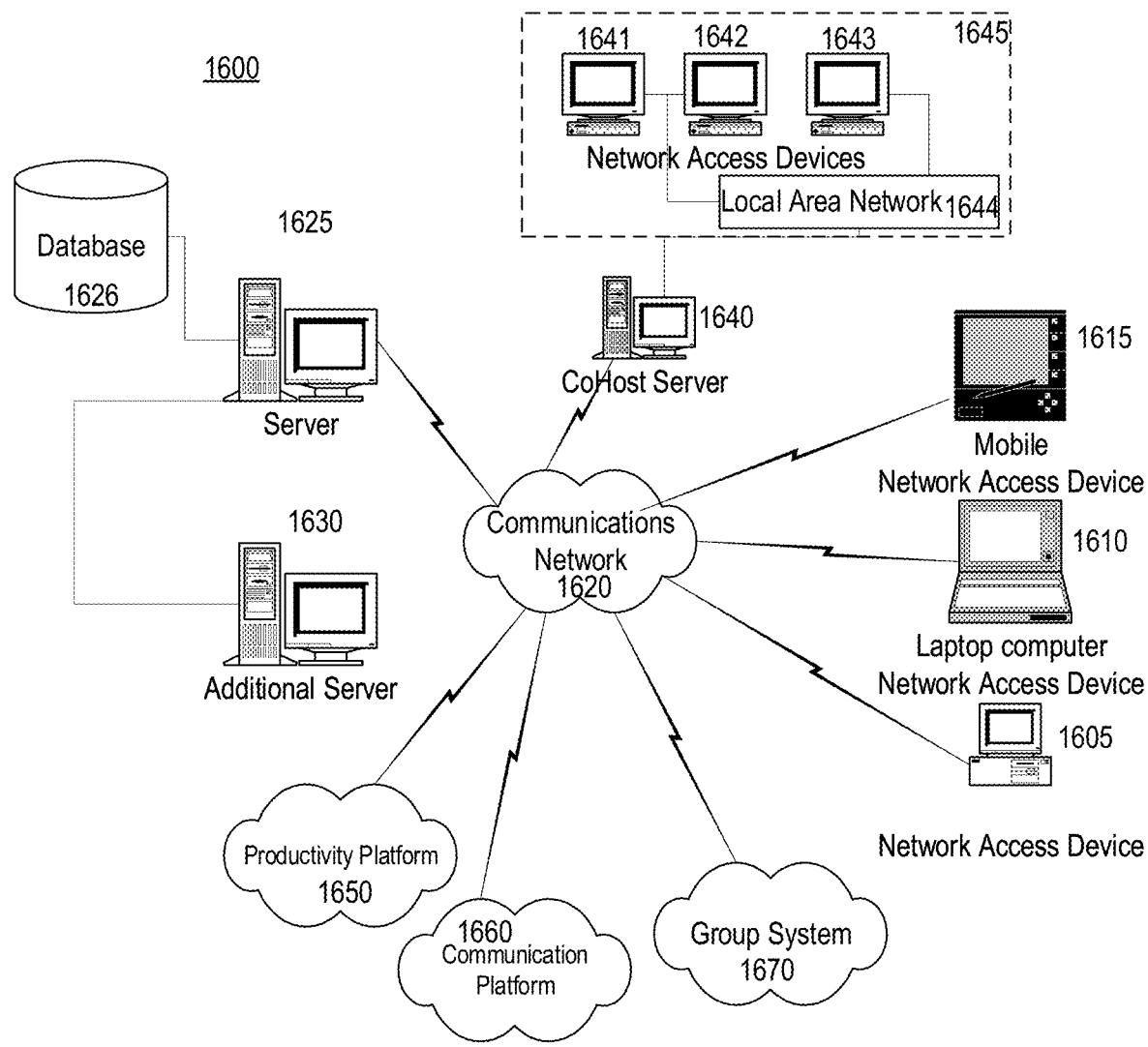
FIG. 16 illustrates an exemplary processing and interface system, according to some embodiments of the present disclosure.

Referring now to FIG. 16, an exemplary processing and interface system 1600 is illustrated. In some aspects, access devices 1615, 1610, 1605, such as a paired portable device 1615 or laptop computer 1610 may be able to communicate with an external server 1625 though a communications network 1620. The external server 1625 may be in logical communication with a database 1626, which may comprise data related to identification information and associated profile information. In some embodiments, the server 1625 may be in logical communication with an additional server 1630, which may comprise supplemental processing capabilities.

In some aspects, the server 1625 and access devices 1605, 1610, 1615 may be able to communicate with a cohost server 1640 through a communications network 1620. The cohost server 1640 may be in logical communication with an internal network 1645 comprising network access devices 1641, 1642, 1643 and a local area network 1644. For example, the cohost server 1640 may comprise a payment service, such as PayPal or a social network, such as Facebook or a LinkedIn.

In some embodiments, the behavioral insight system may integrate or communicate with external systems, such a productivity platform 1650, communication platform 1660, or group system 1670. For example, a communication platform 1660 may allow for instant messaging and provide behavioral insights in real time during communication. As another example, group systems 1670 may comprise enterprise systems, such as within companies, educational institutions, and clubs.

Conclusion

A number of embodiments of the present disclosure have been described. While this specification contains many specific implementation details, these should not be construed as limitations on the scope of any disclosures or of what may be claimed, but rather as descriptions of features specific to particular embodiments of the present disclosure.

Certain features that are described in this specification in the context of separate embodiments can also be implemented in combination or in a single embodiment. Conversely, various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order show, or sequential order, to achieve desirable results. In certain implementations, multitasking and parallel processing may be advantageous. Nevertheless, it will be understood that various modifications may be made without departing from the spirit and scope of the claimed disclosure.

What is claimed is:

1. A method for providing behavioral insights comprising:
receiving at least one psychometric profile and one or more of performance data, an interest list, a skill list, a talent list, and an aspiration list of a subject;
developing subject behavioral insights for the subject based on processing the at least one psychometric profile, the interest list, and the skill list;

building a subject dashboard comprising a visualization of subject behavioral insights;

providing the subject dashboard to a user; and receiving one or more updated aspiration list, updated interest list, updated performance data, updated skill list, or updated talent list, wherein the subject dashboard comprises an animation indicating one or more of a progression of the aspiration list to the updated aspiration list, the interest list to the updated interest list, the talent list to the updated talent list, the skill list to the updated skill list, and the performance data to the updated performance data.

2. The method of claim 1, wherein the user comprises the subject, and the subject's dashboard is customized based on subject behavioral insights.

3. The method of claim 1, further comprising integrating with an external communication system, wherein at least a portion of the subject dashboard is visible when communicating with the subject through the external communication system.

4. The method of claim 1, further comprising one or more:

receiving an aspiration list of the subject, wherein the aspiration list comprises at least one aspiration and date associated with the least one aspiration;

receiving an interest list of the subject, wherein the interest list comprises at least one interest and date associated with the least one interest; and receiving a talent list of the subject, wherein the talent list comprises at least one talent and date associated with the least one talent.

5. A method for providing behavioral insights for a group comprising:

receiving a plurality of psychometric profiles for a group, wherein the group comprises a plurality of group members, and wherein at least one of the plurality of psychometric profiles relates to each group member;

creating a group profile;

receiving a group skill list, wherein a skill list is compiled from group member skill lists;

developing group behavioral insights based at least on processing of the plurality of psychometric profiles; and providing a behavioral insights dashboard comprising a visualization of behavioral insights.

6. The method of claim 5, wherein the group behavioral insights are further based on the group skill list, wherein the plurality of psychometric profiles change as the plurality of group members changes, and wherein group behavioral insights are updated in real time as plurality of group members changes.

7. The method of claim 5, further comprising recommending changes to the plurality of group members based on behavioral insights.

8. The method of claim 7, wherein recommending is based on a balance assessment of group behavioral insights.

9. The method of claim 7, further comprising integrating with an external communication system, wherein at least a portion of one or both group behavioral insights and group member behavioral insights are provided when communicating with one or both the group or group members.

10. A method of sharing behavioral insights comprising:

receiving at least a first psychometric profile of a first subject and a first skill list of the first subject;

developing a first set of behavioral insights based on at least the first psychometric profile and the first skill list;

creating a first subject profile comprising at least a first subject name and the first set of behavioral insights;

generating a first subject dashboard comprising a first visualization of at least a portion of the first set of behavioral insights, wherein the first visualization is provided in a first plurality of segments comprising at least one visualization type;

assigning visibility values to the first plurality of segments, wherein visibility values indicate privacy levels of each of the first plurality of segments;

receiving a first sharing request from a server from the first subject for a second subject, wherein the first sharing request indicates a first threshold visibility value, wherein at least a portion of the first plurality of segments with visibility values below the first threshold visibility value are visible to the second subject; and providing at least a portion of segments from the first subject dashboard to the second subject, wherein at least the portion of segments comprise visibility values less than the first threshold visibility value.

11. The method of claim 10, further comprising:

receiving at least a second psychometric profile of the second subject and a second skill list of the second subject;

developing a second set of behavioral insights based on at least the second psychometric profile and the second skill list;

creating a second subject profile comprising at least a second subject name and the first set of behavioral insights;

generating a second subject dashboard comprising a second visualization of at least a portion of the second set of behavioral insights, wherein the second visualization is provided in a second plurality of segments comprising at least one visualization type;

assigning visibility values to the first plurality of segments and the second plurality of segments, wherein visibility values indicate privacy levels of each of the first plurality of segments and the second plurality of segments;

receiving a second sharing request from the second subject for the first subject, wherein the second sharing request indicates a second threshold visibility value, wherein at least a portion of the second plurality of segments with visibility values below the second threshold visibility value are visible to the first subject; and providing at least a portion of segments from the second subject dashboard to the first subject, wherein at least the portion of segments comprise visibility values less than the second threshold visibility value.

12. The method of claim 11, wherein the first threshold visibility value and the second threshold visibility value are different.

13. The method of claim 10, further comprising integrating with an external communication system.

14. The method of claim 13, wherein at least a portion of the portion of segments of the first set of behavioral insights is visible to the second subject when the second subject communicates with the first subject through the external communication system.

* * * * *